United States Patent
Talmadge

(10) Patent No.: US 10,694,691 B2
(45) Date of Patent: Jun. 30, 2020

(54) INTERGENERIC HYBRID PLANTS AND METHODS OF PRODUCTION

(71) Applicant: FLORANOVA SERVICE CORP, Lompoc, CA (US)

(72) Inventor: Paul Andrew Talmadge, Santa Maria, CA (US)

(73) Assignee: Floranova Service Corporation, Lompoc, CA (US)

( * ) Notice: Subject to any disclaimer, the term of this patent is extended or adjusted under 35 U.S.C. 154(b) by 335 days.

(21) Appl. No.: 15/613,761

(22) Filed: Jun. 5, 2017

(65) Prior Publication Data

US 2018/0343817 A1 Dec. 6, 2018

(51) Int. Cl.
*A01H 6/14* (2018.01)
*A01H 1/02* (2006.01)

(52) U.S. Cl.
CPC ............ *A01H 1/02* (2013.01); *A01H 6/14* (2018.05); *A01H 6/1496* (2018.05)

(58) Field of Classification Search
CPC ..................................................... A01H 6/14
See application file for complete search history.

(56) References Cited

U.S. PATENT DOCUMENTS 5,523,520 A 12/1996 Hunsperger et al.
7,223,909 B2 * 5/2007 Hauptmann ......... C12N 15/825
800/323

OTHER PUBLICATIONS

Olorode et al Brittonia vol. 22, pp. 359-369 (Year: 1970).*
Christov Helia vol. 36, No. 58, pp. 1-18 (Year: 2013).*
He et al Molecular Breeding vol. 26, pp. 19-29 (Year: 2010).*
Lou et al Euphytica vol. 174, pp. 91-103 (Year: 2010).*
Anantasaran, J. et al., "Cytogenetic characterization of *Zinnia* species and cultivars", Floriculture and Ornamental Biotechnology, 2007, 1:125-130.
Boyle, T. H. and Stimart, D.P., "Interspecific hybrids of *Zinnia elegans* jacq. and *Z. angustifolia* hbk: Embryology, morphology and powdery mildew resistance", Euphytica, 1982, 31:857-867.
Eshed, Y. and Zamir, D., "Less-than-additive epistatic interactions of quantitative trait loci in tomato", *Genetics*, 1996, 143:1807-1817.
Godoy-Hernández, G., and Miranda-Ham, M., "Marigold biotechnology: Tissue culture and genetic transformation", Transgenic Plant Journal, 2007, 1:169-174.
Kraft, T., Hansen, M., and Nilsson, N.O., "Linkage disequilibrium and fingerprinting in sugar beet", *Theor. Appl. Genet.*, 2000, 101:323-326.
Priyanka, D., Shalini, T. and Navneet, V.K., "A brief study on marigold (*Tagetes* species): A review", IRJP, 2013, 4:43-48.
Robleto, G. A. and Ascher, P.D., "Congruity backcrossing: A method to reverse isolation", Annu. Rep. Bean Improv. Coop., 1996, 39:122-123.
Zhang, P. et al., "Karyotype studies on *Tagetes erecta* L. and *Tagetes patula* L.", African Journal of Biotechnology, 2011, 10:16138-16144.

* cited by examiner

*Primary Examiner* — David H Kruse
(74) *Attorney, Agent, or Firm* — Jondle & Associates, P.C.

(57) ABSTRACT

The present invention relates to intergeneric hybrid plants of *Zinnia elegans* and *Tagetes erecta* and methods for making the same. The invention further relates to methods for producing intergeneric hybrid plants of *Z. elegans* and *T. erecta* containing in their genetic material one or more transgenes and the intergeneric hybrid plants produced by that method. The invention also relates to transferring desirable characteristics from one genera to the other, as well as creation of new unique characteristics not found in either of the parent genera alone. The invention further relates to methods for producing intergeneric hybrid plants of *Z. elegans* and *T. erecta* derived from intergeneric hybrid plants of *Z. elegans* and *T. erecta* and to the plants produced by the method.

10 Claims, No Drawings

INTERGENERIC HYBRID PLANTS AND METHODS OF PRODUCTION

BACKGROUND OF THE INVENTION

The present invention relates to methods for producing intergeneric hybrid plants from crosses between *Zinnia elegans* and *Tagetes erecta* and to the plants produced by the methods. All publications cited in this application are herein incorporated by reference.

*Zinnia* is a genus of plants of the sunflower tribe within the daisy family, Asteraceae, containing approximately 23 different species. Zinnias are annuals, shrubs, and sub-shrubs native to scrub and dry grassland areas in North America, with some species in Central and South America. *Zinnia* are popular garden flowers that are recognized for their solitary, long-stemmed flowers having a range of appearances that come in a variety of bright colors and ability to withstand hot summer temperatures.

*Zinnia elegans*, also known as *Zinnia violacea*, common zinnia or elegant *zinnia*, is the most familiar *zinnia* species. *Z. elegans* is an annual flowering plant native to Mexico, but grown as an ornamental plant and naturalised in many places. There are hundreds of *Z. elegans* cultivars available that come in many different sizes, forms and flower colors, such as red, yellow, orange, pink, rose, lavender, green and white. The solitary flower heads are typically about two inches across, although there are giant forms up to six inches across, with the purple ray florets surrounding black and yellow discs and lanceolate leaves opposite the flower heads. *Z. elegans* are susceptible to powdery mildew, particularly in humid climates, as well as to bacterial and fungal leaf and flower spot, as well as *alternaria* blight.

*Tagetes* is a genus of mostly herbaceous plants in the daisy family, Asteraceae, containing approximately 50 different species usually known as marigolds. *Tagetes* are annuals or perennials native to North and South America, with some species having become naturalized around the world. The flowers of *Tagetes* naturally occur in golden, orange, yellow, and white colors, sometimes with maroon highlights. Most species have pinnate green leaves, and many species have foliage with a musky, pungent scent that is said to deter some common insect pests and nematodes. Marigolds produce a substance called alpha-terthienyl, which can aid in the reduction of root-knot nematodes and other disease promoting organisms, such as fungi, bacteria, insects and some viruses. Marigolds are often used as companion plants in gardens to repel insect pests from neighboring plants.

*Tagetes erecta*, also known as African marigold, Mexican marigold, Aztec marigold, American marigold and big marigold, is an annual flowering plant native to Mexico and Central America. Mexican marigolds are tall, erect-growing plants up to four feet in height with large, globe-shaped flowers of two to four inches diameter in shades primarily of yellow and orange. *T. erecta* is a medicinal and ornamental plant and is used for its nematocide, cosmetic and medicinal properties. The essential oil of the *T. erecta* flower contains antioxidants and is used as a nutritional supplement. Additionally, the florets of *T. erecta* are rich in the orange-yellow carotenoid lutein and are used as a food color. *T. erecta* is widely cultivated commercially with many cultivars in use as ornamental plants and for the cut-flower trade.

Interspecific hybridization has been carried out in cultivated plants as a means to increase genetic variability and introduce valuable traits of one species into another. Interspecific hybridization is considered to be one of the most useful strategies to develop new cultivars. However, there are natural processes that ensure reproductive isolation of distinct species, and the ability of any two species to create viable interspecific hybrid seeds or plants is unpredictable and often has proved impossible. Rare interspecific hybrids have been produced from *Z. elegans*×*Z. angustifolia*, but embryo culture had to be employed and the hybrids were sterile. Interspecific hybrids between *T. erecta* and *T. patula* (French marigold) are available, but result in a sterile, triploid plant that is unable to reproduce.

Intergeneric hybridization, the crossing of two plants from different genera, is more uncommon, unpredictable and improbable than interspecific hybridization because the genetic distance is greater between genera than between species. Only a few successful intergeneric hybrids have been reported and they are frequently only possible through human intervention and the use of embryo rescue.

Thus, it is desirable to create new hybrids having novel characteristics. The present invention provides intergeneric hybrid plants of *Z. elegans* and *T. erecta* and methods for creating intergeneric hybrid plants of *Z. elegans* and *T. erecta* having more varied color and improved plant habit, improved disease resistance, summer performance and heat tolerance, as well as other desirable characteristics. Prior to the present invention, there have been no previous reports of hybridization between *Zinnia* spp. and *Tagetes* spp.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and not limiting in scope. In various embodiments, one or more of the above-described problems have been reduced or eliminated, while other embodiments are directed to other improvements.

According to the invention, there are provided novel intergeneric hybrid plants of *Zinnia elegans* and *Tagetes erecta*. This invention thus relates to the seeds of intergeneric hybrid plants of *Z. elegans* and *T. erecta*, to the plants and plant parts of intergeneric hybrid plants of *Z. elegans* and *T. erecta*, and to methods for producing intergeneric hybrid plants of *Z. elegans* and *T. erecta*. The invention further relates to methods for producing intergeneric hybrid plants of *Z. elegans* and *T. erecta* containing in their genetic material one or more transgenes, and to the transgenic intergeneric hybrid plants of *Z. elegans* and *T. erecta* produced by that method. The invention relates to using either *Z. elegans* or *T. erecta* as the female or male parent.

The method of the present invention producing intergeneric hybrid plants of *Z. elegans* and *T. erecta* was surprising and unexpected. Prior to the present invention, there were no reports of intergeneric hybrid plants of *Z. elegans* and *T. erecta* seen in nature and there were no reports of other breeders attempting to make the intergeneric hybrid plants, likely due to compatibility issues between genera.

In another aspect, the invention provides a method to produce intergeneric hybrid plants of *Z. elegans* and *T. erecta* in which the pollination technique comprised collecting pollen from open male flowers and applying the pollen to receptive (open) female flowers on the female indicated in the cross. At mature harvest, the flower head is cut and dried fully before being broken open and seeds cleaned out for further use and for growing intergeneric hybrid plants. In a further aspect, *Z. elegans*×*T. erecta* and *T. erecta*×*Z. elegans* crosses were set up using the nuclear male sterile available in both genera.

In a further aspect of the invention, the intergeneric cross is used as a way to transfer characteristics like disease resistance from *T. erecta* to *Z. elegans*, and to move novel flower colors like red and purple from *Z. elegans* to *T. erecta* and cream from *T. erecta* to *Z. elegans*. In another aspect of the invention, the intergeneric combination of *Z. elegans* and *T. erecta* results in totally new unique traits, such as a vase shaped and branched plant habit, abnormal flower petals and an abnormal floral center, that are not present in either of the parent plant species.

Another aspect of the invention is to provide methods for producing other intergeneric hybrid plants of *Z. elegans* and *T. erecta* derived from intergeneric hybrid plants of *Z. elegans* and *T. erecta*. In a further aspect, the intergeneric hybrid plants of *Z. elegans* and *T. erecta* are used in additional crosses to *Z. elegans* plants, *T. erecta* plants or other intergeneric hybrid plants of *Z. elegans* and *T. erecta* to produce further intergeneric hybrid plants of *Z. elegans* and *T. erecta*. The invention relates to using intergeneric hybrid plants of *Z. elegans* and *T. erecta*, *Z. elegans* or *T. erecta* as the female or male parent.

Another aspect of the present invention provides a method of producing an intergeneric hybrid seed of *Z. elegans* and *T. erecta* comprising:
(a) selecting a first plant of *Z. elegans* or *T. erecta* to use as the female parent and a second plant of the other genera to use as the male parent;
(b) collecting pollen from open flowers on the male parent;
(c) applying the pollen to receptive female flowers on the female parent indicated in the cross to produce intergeneric hybrid seed;
(d) harvesting intergeneric hybrid seed of *Z. elegans* and *T. erecta*.

Another aspect of the present invention comprises a method of producing an intergeneric hybrid plant of *Z. elegans* and *T. erecta* comprising:
(a) selecting a plant of *Z. elegans* or *T. erecta* to use as the female parent and a plant of the other genera to use as the male parent in a cross;
(b) collecting pollen from open flowers on the male parent;
(c) applying the pollen to receptive female flowers on the female parent indicated in the cross;
(d) isolating an embryo resulting from the cross by embryo rescue; and
(e) growing said embryo to obtain an intergeneric hybrid plant of *Z. elegans* and *T. erecta*.

Another aspect of the invention relates to an intergeneric hybrid plant of *Z. elegans* and *T. erecta* or plant part thereof vegetatively propagated from an intergeneric hybrid plant of *Z. elegans* and *T. erecta*.

In another aspect of the invention, the *Z. elegans*, *T. erecta*, or intergeneric hybrid plant of *Z. elegans* and *T. erecta* plant used as the female parent is nuclear male sterile.

In another aspect of the invention, the intergeneric hybrid plants have different flower colors or color patterns when compared to a *Z. elegans* or *T. erecta* plant.

In another aspect of the invention, the intergeneric hybrid plants have a different plant habit when compared to a *Z. elegans* or *T. erecta* plant.

In another aspect of the invention, the intergeneric hybrid plants have improved disease resistance when compared to a *Z. elegans* plant.

In another aspect, the present invention provides for single gene or multiple gene converted plants of intergeneric hybrid plants of *Z. elegans* and *T. erecta*. In another aspect, the present invention provides for single gene or multiple gene converted plants of the parents of intergeneric hybrid plants of *Z. elegans* and *T. erecta*. The single or multiple transferred gene(s) may preferably be a dominant or recessive allele. The single or multiple transferred gene(s) will confer such traits as herbicide resistance, insect resistance, resistance to bacterial, fungal, or viral diseases, male fertility, male sterility, enhanced nutritional quality, and industrial usage. The single or multiple gene(s) may be a naturally occurring *Z. elegans* and *T. erecta* gene or a transgene introduced through genetic engineering techniques.

In another aspect, the present invention provides regenerable cells for use in tissue culture of intergeneric hybrid plants of *Z. elegans* and *T. erecta*. The tissue culture will preferably be capable of regenerating plants having the physiological and morphological characteristics of the foregoing intergeneric hybrid plants of *Z. elegans* and *T. erecta*, and of regenerating plants having substantially the same genotype as the foregoing intergeneric hybrid plants of *Z. elegans* and *T. erecta*. Genetic variants of intergeneric hybrid plants of *Z. elegans* and *T. erecta* naturally generated through the use of tissue culture or artificially induced utilizing mutagenic agents during tissue culture are aspects of the present invention. Preferably, the regenerable cells in such tissue cultures will be embryos, protoplasts, meristematic cells, callus, pollen, cotyledon, leaves, flowers, anthers, roots, pistils, root tips, glumes, seeds, panicles or stems. Still further, the present invention provides intergeneric hybrid plants of *Z. elegans* and *T. erecta* regenerated from the tissue cultures of the invention.

In addition to the exemplary aspects and embodiments described above, further aspects and embodiments will become apparent by study of the following descriptions.

DETAILED DESCRIPTION OF THE INVENTION

In the description and tables that follow, a number of terms are used. In order to provide a clear and consistent understanding of the specification and claims, including the scope to be given such terms, the following definitions are provided:

Allele. The allele is any of one or more alternative form of a gene, all of which relate to one trait or characteristic. In a diploid cell or organism, the two alleles of a given gene occupy corresponding loci on a pair of homologous chromosomes.

Amiprophos-methyl (APM). As used herein, amiprophos-methyl (APM) refers to a compound used in plant breeding to induce chromosome doubling.

Androecium. Male parts of a plant flower which are collectively termed the stamens, which are the pollen-producing reproductive organ of a flower.

Allotetraploid. As used herein, allotetraploid means a plant that is diploid for two genomes, each from a different species.

Allotriploid. As used herein, allotriploid means a triploid plant having three times the monoploid chromosome number.

Aneu-tetraploid. As used herein, aneu-tetraploid means a tetraploid plant and any plant having more or less than four times the monoploid chromosome number.

Aneu-triploid. As used herein, aneu-triploid means a triploid plant and any plant having more or less than three times the monoploid chromosome number.

Anti-mitotic agent. As used herein, anti-mitotic refers to a compound or chemical that is used to block cell growth by stopping mitosis (cell division) used in plant breeding to induce chromosome doubling. Examples of anti-mitotic agents include, but are not limited to, colchicine, trifluralin, oryzalin, and amiprophos-methyl (APM).

Asexual propagation/Asexual reproduction. Asexual propagation or asexual reproduction means every type of plant propagation except for sexually produced seeds. Examples of asexual propagation include, but are not limited to, cuttings, grafting, division, apomixis, or regeneration in tissue culture.

Backcrossing. Backcrossing is a process in which a breeder repeatedly crosses hybrid progeny back to one of the parents, for example, a first generation hybrid $F_1$ with one of the parental genotype of the $F_1$ hybrid.

Cell. As used herein, cell includes a plant cell, whether isolated, in tissue culture, or incorporated in a plant or plant part.

Chimera. A chimera or a chimeric plant is a plant that consists of two or more genetically distinct groups of cells. The genetic distinctness usually originates from a mutation.

Chromosome number. The characteristic number of chromosomes found in the cell nuclei of organisms of a particular species. Most eukaryotes are diploid, meaning they have two sets of chromosomes in a cell (2n; a pair of each chromosome).

Chromosomal stability. As used herein, chromosomal stability refers to a chromosome that is not subject to sudden or extreme change or fluctuation.

Colchicine. Colchicine is a pale-yellow alkaloid, $C_{22}H_{25}NO_6$, obtained from the autumn *crocus* and used in plant breeding to induce chromosome doubling.

Congruity backcrossing (CBC). Congruity backcrossing involves making a primary cross, A×B→C, and the resulting hybrid (C) is then utilized to cross back to one of the original parents (A or B; also known as recurrent parents) each cycle in an alternating fashion.

Crossing. The pollination of a female flower of a plant, thereby potentially resulting in the production of seed from the flower.

Cross-pollination. Fertilization by the union of two gametes from different plants.

Cutting. A part originating from a plant, such as a stem, leaf, or root, removed from a plant to propagate a new plant, as through rooting or grafting.

Diploid. A diploid (denoted by the somatic cell chromosome number 2n=2x) is a somatic cell or plant having one pair of each type of chromosome (homologous pair), so that the basic (monoploid) chromosome number (denoted by the symbol x) is doubled.

Dominant inheritance. Refers to a mode of inheritance in which the phenotype of a certain characteristic or trait is determined by a dominant allele.

Dominant mutation. Refers to the allele of a gene expressed in the phenotype of a heterozygote; the non-expressed allele is recessive. Also refers to the phenotype associated with a dominant allele. One copy of a dominant mutant allele leads to a mutant phenotype.

Emasculate. The removal of plant male sex organs or the inactivation of the organs with a chemical agent or a cytoplasmic or nuclear genetic factor conferring male sterility.

Embryo. A young sporophyte of a seed plant usually comprising a rudimentary plant with plumule, radicle and cotyledons, which begins as a developing egg-cell formed after fertilization.

Embryo culture. The growth of isolated plant embryos on suitable media in vitro.

Embryo rescue. As used herein, embryo rescue is the process plant breeder's use to attempt to germinate embryos that may be weak, immature, or would otherwise not develop into a mature viable seed on the parent plant. For example, one form of embryo rescue is ovule culture, which involves aseptically removing the ovule from the seed and placing the ovule onto artificial media to enable the embryo to germinate and grow into a plant.

$F_{\#}$. The "F" symbol denotes the filial generation, and the # is the generation number, such as $F_1$, $F_2$, $F_3$, etc.

$F_2$. The "$F_2$" symbol denotes the offspring resulting from the selfing or self-mating of members of the first generation, the $F_1$ generation.

Gamete. A cell or nucleus that may participate in sexual fusion to form a zygote.

Gene. As used herein, gene refers to a segment of nucleic acid. A gene can be introduced into a genome of a species, whether from a different species or from the same species, using transformation or various breeding methods.

Genotype. Refers to the genetic constitution of a cell or organism.

Gynoecium. The ovule producing parts of a plant's flower.

Haploid. A haploid is a cell nucleus containing only one representative of each chromosome of the chromosome complement, denoted by the symbol n. The haploid number (n) is the number of chromosomes in a haploid cell nucleus. Gametes are haploid cells.

Heterosis. Also called hybrid vigor. The tendency of a crossbred plant to show qualities superior to those of both parents.

Heterozygous. Refers to a genetic constitution in which the corresponding alleles of a certain gene locus are different.

Homozygous. Refers to a genetic constitution in which the corresponding alleles of a certain gene locus are identical.

Inbreeding. Is defined as the production of offspring by the fusion of genetically closely related gametes.

Inflorescence. A group or cluster of flowers arranged on a stem that is composed of a main branch or an arrangement of branches.

Intergeneric cross. Intergeneric cross means the sexual hybridization of two individuals, each from a different genus.

Intergeneric hybrid. An intergeneric hybrid of the present invention is produced by a cross between plants in two different genera.

Intergeneric hybrid seed or plants of *Z. elegans* and *T. erecta*. Refers to seed or plants produced by the method of the present invention that are intergeneric hybrid combinations of *Zinnia elegans* and *Tagetes erecta*, where either genus may be used as the male or female parent, as well as seed or plants produced by further crosses of intergeneric hybrid plants of *Z. elegans* and *T. erecta* to other intergeneric hybrid plants of *Z. elegans* and *T. erecta*, or to other plants of *Z. elegans* or *T. erecta*.

Interspecific cross. Interspecific cross means the sexual hybridization of two individuals, each from different species of the same genus.

Interspecific hybrid. Interspecific hybrid means a plant of the $F_1$ generation resulting from an interspecific cross or a cross between two different species.

Karyotype analysis. As used here, karyotype analysis means the ascertainment of chromosome number and constitution by light microscopy analysis of stained metaphase chromosomes. Cells are collected, induced to divide, and then arrested at metaphase (a stage of cell division when the chromosome are condensed and therefore visible). The chromosomes are stained with certain dyes that show a pattern of light and dark bands. Large changes in chromosomes can be detected using karyotype analysis.

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A locus confers one or more traits such as, for example, herbicide tolerance, insect resistance, disease resistance, flower color, flower shape, plant height, etc. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

$M_0$. The $M_0$ generation is the generation treated with a mutagen. Subsequent generations are designated $M_1$, $M_2$, $M_3$, etc.

Monoploid. The monoploid chromosome number is the number of chromosomes in a single (non-homologous) set (x) and can be different from the haploid (n) number.

Multiple Gene Converted (Conversion). Multiple gene converted (conversion) includes plants developed by a plant breeding technique called backcrossing wherein essentially all of the desired morphological and physiological characteristics of an inbred are recovered, while retaining two or more genes transferred into the inbred via crossing and backcrossing. The term can also refer to the introduction of multiple genes through genetic engineering techniques known in the art.

Mutation. Mutations are changes in the DNA sequence of a cell's genome and are caused by mutagens, like radiation or chemicals, as well as by errors that occur spontaneously during DNA replication.

Oryzalin. As used herein, oryzalin refers to a compound used in plant breeding to induce chromosome doubling.

Outbreeding. Also known as outcrossing, is the practice of introducing unrelated genetic material into a breeding line by crossing between unrelated or distantly related individuals. Outbreeding is the opposite of inbreeding.

Ovule culture. The culture of excised ovules on suitable media in vitro.

Percent Identity. Percent identity as used herein refers to the comparison of the homozygous alleles of two plants. Percent identity is determined by comparing a statistically significant number of the homozygous alleles of two developed plants.

Percent Similarity. Percent similarity as used herein refers to the comparison of the homozygous alleles of one plant with another plant, and if the homozygous allele of both plants matches at least one of the alleles from the other plant then they are scored as similar. Percent similarity is determined by comparing a statistically significant number of loci and recording the number of loci with similar alleles as a percentage.

Phenotype. Refers to any observable characteristic or trait of a plant, such as flower color, plant size, etc.

Plant. As used herein, the term plant includes reference to an immature or mature whole plant, including a plant from which seed or anthers have been removed. Seed or embryo that will produce the plant is also considered to be the plant.

Plant cell. Plant cell, as used herein includes plant cells whether isolated, in tissue culture, or incorporated in a plant or plant part.

Plant habit. This is a visual assessment of the overall growth phenotype of the plant.

Plant hormone composition. As used herein, a plant hormone composition refers to a chemical that regulates plant growth. For example, Indole-3-butyric acid, $N^6$-benzyl adenine, and gibberellic acid.

Plant part. As used herein, the term "plant part" includes protoplasts, leaves, stems, roots, root tips, anthers, pistils, seed, embryo, pollen, ovules, cotyledon, hypocotyl, cyathium, bract, shoot, tissue, petiole, cells and meristematic cells, and the like.

Pollination. Pollination is the process by which pollen is transferred in plants, thereby enabling fertilization and sexual reproduction.

Polyploid. An individual plant carrying more than two complete sets of homologous chromosomes.

Post-production. Post-production means the time after leaving the greenhouse production facility.

Post-production performance. Post-production performance relates to plant quality and the subsequent deterioration in quality from the time it leaves the greenhouse production facility.

Progeny. As used herein, progeny includes an $F_1$ plant produced from the cross of two plants. Progeny further includes, but is not limited to, subsequent $F_2$, $F_3$, $F_4$, $F_5$, $F_6$, $F_7$, $F_5$, $F_9$, and $F_{10}$ generational crosses with the parents and between the progeny.

Receptive flowers. Refers to flowers that are open and ready for pollination.

Recessive inheritance. Refers to a mode of inheritance in which the phenotype of a certain characteristic or trait is determined by a recessive allele.

Recessive mutation. The phenotype of a recessive mutation is visible only in a homozygous genotype.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Sexual propagation/Sexual reproduction. Refers to the propagation of plants from seeds.

Single gene converted. Single gene converted or conversion plant refers to plants which are developed by a plant breeding technique called backcrossing or via genetic engineering wherein essentially all of the desired morphological and physiological characteristics of a line are recovered in addition to the single gene transferred into the line via the backcrossing technique or via genetic engineering.

Somatic cell. Any cell of a plant other than the spores, gametes, or their precursors.

Stamen. The pollen-producing reproductive organ of a flower.

Tetraploid. As used herein, tetraploid refers to a cell or plant having a chromosome number that is four times the monoploid number of chromosomes and is designated in somatic cells by 2n=4x.

Transgene. A genetic sequence which has been introduced into the nuclear or chloroplast genome of a plant by a genetic transformation technique.

Trifluralin. As used herein, trifluralin refers to a compound used in plant breeding to induce chromosome doubling.

Triploid. As used herein, a triploid refers to a cell or plant having a chromosome number that is three times the monoploid number of chromosomes and is designated in somatic cells by 2n=3x.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants).

The following detailed description is of the currently contemplated modes of carrying out the invention. The description is not to be taken in a limiting sense, but is made merely for the purpose of illustrating the general principles of the invention, since the scope of the invention is best defined by the appended claims.

Production of Intergeneric Hybrid Plants of *Z. elegans* and *T. erecta*

The present invention was unexpectedly produced during a poly cross involving *Berlandiera lyrata*, *Zinnia elegans* and *Tagetes erecta*. All possible combinations were made in the crossing block in an effort to find a compatible genus to cross with *Berlandiera* to improve it and transfer the chocolate scent from *Berlandiera* to a more ornamental plant. All crosses made utilized the standard nomenclature for breeding where the female parent (seed parent) is stated first and male parent (pollen parent) second. During the poly cross, the following crosses were made with the abbreviations of *B. lyrata*=B (6 plants), *T. erecta*=T (10 plants) and *Z. elegans*=Z (10 plants):
  a) B×T
  b) T×B
  c) B×Z
  d) Z×B
  e) T×Z
  f) Z×T Additionally, seed was produced on the maintainer lines of *Tagetes* and *Zinnia* to ensure there was a control to verify that seed set conditions were working. Ten female flowers of each crossing were pollinated in this round of pollination.

Out of this crossing block of 26 plants, unexpectedly one cross combination produced seed, which was the cross *Z. elegans*×*T. erecta*.

Breeding Method to Produce Intergeneric Hybrid Plants of *Z. elegans* and *T. erecta*

For pollination of both *Zinnia* and *Tagetes*, pollen was collected from open male flowers and applied to receptive (open) female flowers on the female indicated in the cross. These pollinated females were further pollinated if needed, such as two or more times per week. The female flower took about 3-4 weeks from pollination to become mature and ready to harvest, depending on climate conditions. At harvest, the flower head was cut and dried fully before being broken open and seeds were obtained for further use and planting to produce intergeneric hybrid plants of *Z. elegans* and *T. erecta*.

When the progeny were grown the first time, parents of both *T. erecta* and *Z. elegans* were grown in the same area of enclosed greenhouses as controls at all stages from germination to growing, flower initiation, and pollination. Surprisingly, the seed of the intergeneric hybrids germinated very well and the plants were earlier to flower than either parent from sowing. The $F_1$ hybrid *Z. elegans*×*T. erecta* germinated 2 days earlier than the control of *Z. elegans* and also opened its initial flowers 10 days earlier than the control plants of *Z. elegans*. Hybridity was confirmed by the appearance of the flower color and/or plant habit being different than the uniform parent lines used for the crosses, as further shown in Tables 1, 3 and 4, as well as by flow cytometry, as shown in Table 5. More than one female line was used to show diversity and that the ability to make this cross was not genotype dependent.

Embryo rescue may be utilized in the method of the present invention. Embryo rescue can be an important, and sometimes absolutely necessary step to accomplish wide crosses in plants. Embryo rescue involves making the desired cross in situ by whatever means needed, whether it is in a traditional sense by applying mature dehisced pollen to a receptive stigma, or by making more efforts to prepare the prospective female by excising the stigma or utilizing chemicals to disable the self-incompatibility systems that may be in place genetically. Once pollination and fertilization is accomplished, the fertilized embryo (ovule) is excised and matured to eventually become a viable plant using standard tissue culture techniques.

Additional Breeding to Verify Results of Intergeneric Hybrid Plants of *Z. elegans* and *T. erecta*

Using the control lines of *Z. elegans* and *T. erecta*, a second round of crossing was done to confirm the first round of crosses were in fact real and the results could be duplicated.

T×Z and Z×T were set up in crosses using the nuclear male sterile in both genera as female parents. This round of crossing was able to confirm the unexpected results of making *Z. elegans*×*T. erecta*, as well as making the intergeneric hybrid in the reciprocal direction of *T. erecta*×*Z. elegans*. Both crosses produced viable $F_1$ intergeneric hybrid seeds that produced viable flowering plants utilized for the breeding process.

Surprisingly, when *Z. elegans* was used as the female parent in the cross, the intergeneric hybrid plants looked primarily like *zinnia*; however, there were subtle differences shown that were not at all like *zinnia*, such as abnormal flower petals and an abnormal floral center that was more similar to marigold. A similar result was observed when *T. erecta* was used as the female parent in the cross, with the intergeneric hybrid plants looking primarily like marigold. The biggest factor in phenotype expression in the intergeneric hybrids seemed to be what the female used in the cross looked like, or its phenotype.

The method of the present invention producing intergeneric hybrid plants of *Z. elegans* and *T. erecta* was surprising and unexpected. Prior to the present invention, there were no reports of intergeneric hybrid plants of *Z. elegans* and *T. erecta* seen in nature and there were no reports of other breeders attempting to make the intergeneric hybrid plants, likely due to compatibility issues between genera. In fact, there were no reasons for a person of ordinary skill in the art to attempt to produce intergeneric hybrid plants of *Z. elegans* and *T. erecta* given the lack of a reasonable expectation of success due to the expected hurdles and known difficulties in making intergeneric crosses and producing viable intergeneric hybrid plants.

Further Breeding of Intergeneric Hybrid Plants of *Z. elegans* and *T. erecta*

The method of the present invention involves the novel crossing of the genera *Zinnia* and *Tagetes* resulting in the unexpected production of seed and fertile offspring. A breeding program was established to utilize this new method as a way to transfer traits such as disease resistance from *T. erecta* into *Z. elegans*, and to move flower colors like red and purple from *Z. elegans* into *T. erecta*.

Numerous new and different traits have unexpectedly emerged from the production of intergeneric hybrid plants of *Z. elegans* and *T. erecta*, including new flower colors and patterns such as tri color flowers, new plant habits such as prostrate habit, and other new traits, such as genetic abnormalities and strange phenotypes like abnormal flower petals, abnormal floral centers and abnormal branching habits that were likely a result of transgressive segregation of genes resulting from the intergeneric cross combination and are not represented in the original parent plant species. Deleterious combinations that confer complete sterility and albino expression have also been seen in the intergeneric hybrids. Additionally, the intergeneric hybrid plants of the present invention have shown strong heterosis for germination (intergeneric hybrids germinate 2 days faster than parent genera), flowering (intergeneric hybrids flower 1-2 weeks quicker than parent genera), flower colors (wide range of colors not present in parent genera) and plant habits (very strong basal branching not seen in parent genera).

The genera *Zinnia* and *Tagetes* are very different and distinct, especially in flower form and color, as well as in resistance to diseases. Both *Zinnia* and *Tagetes* are genera that can set self-seed and also have a genetic male sterile gene, also known as nuclear male sterile. The nuclear male sterile condition confers the absence of male flower parts and is linked with the absence of petals, a condition known as apetalous (ap). The male sterile gene is a single recessive gene in *Z. elegans* and *T. erecta*. Nuclear male sterility is often limited by maintenance of multiple lines, partial and unstable male sterility and limited fertility restoring gene sources, all of which restrict the benefits of hybrid plants. The present invention overcame these hurdles in that the nuclear male sterile gene was "fixed" in female lines and maintained at a rate of 50% male steriles for each generation grown. When the genera *Zinnia* and *Tagetes* were crossed, and these "fixed" female lines were used on both sides, the $F_1$ hybrid populations and subsequent generations also segregated with 50% male sterile segregation per generation.

Examples of Intergeneric Hybrid Plants of *Z. elegans* and *T. erecta* Produced by the Method of the Invention Table 1 shows over 200 examples of intergeneric hybrid plants of *Z. elegans* and *T. erecta* produced by the method of the invention in 2014 and the parent plants used in the crosses. Column 1 shows the genus and species of the female parent, column 2 shows the name of the female parent, column 3 shows a brief description of the female parent, column 4 shows the genus and species of the male parent, column 5 shows the name of the male parent, column 6 shows a brief description of the male parent, column 7 shows the name of the *Z. elegans* and *T. erecta* intergeneric hybrid produced in the cross and column 8 shows a brief description of the intergeneric hybrid plant. In Table 1, "m" indicates that a mass of plants was made for pollination and harvest of seed, and "ms" indicates male sterile. When a color is listed, it indicates the flower color. All parent plants used for crossing listed in Table 1 segregated for the male sterile (ms) condition, as described above.

TABLE 1

| Female parent genus species | Female parent name | Description of female parent | Male parent genus species | Male parent name | Description of male parent | Intergeneric hybrid name | Description of intergeneric hybrid |
|---|---|---|---|---|---|---|---|
| Z. elegans | 78-11 | gold-red bicolor, ms | T. erecta | 1653 | white | 8191-1 | dwarf, white |
| Z. elegans | 78-11 | gold-red bicolor, ms | T. erecta | 1653 | white | 8191-2 | dwarf, white |
| Z. elegans | 78-11 | gold-red bicolor, ms | T. erecta | 1653 | white | 8191-3 | dwarf, white |
| Z. elegans | 78-11 | gold-red bicolor, ms | T. erecta | 1653 | white | 8191-4 | dwarf, white |
| Z. elegans | 78-11 | gold-red bicolor, ms | T. erecta | 1653 | white | 8191-5 | dwarf, white |
| Z. elegans | 78-11 | gold-red bicolor, ms | T. erecta | 1653 | white | 8191-6 | dwarf, white |
| Z. elegans | 78-11 | gold-red bicolor, ms | T. erecta | 1653 | white | 8191-7 | dwarf, white |
| Z. elegans | 78-11 | gold-red bicolor, ms | T. erecta | 1653 | white | 8191-8 | dwarf, white |
| Z. elegans | 78-11 | gold-red bicolor, ms | T. erecta | 1653 | white | 8191-9 | dwarf, white |
| Z. elegans | 78-11 | gold-red bicolor, ms | T. erecta | 1653 | white | 8191-10 | semi-dwarf, white |
| Z. elegans | 78-11 | gold-red bicolor, ms | T. erecta | 1653 | white | 8191-11 | semi-dwarf, white |
| Z. elegans | 78-11 | gold-red bicolor, ms | T. erecta | 1653 | white | 8191-12 | semi-dwarf, white |
| Z. elegans | 78-11 | gold-red bicolor, ms | T. erecta | 1653 | white | 8191-13 | semi-dwarf, white |
| Z. elegans | 78-11 | gold-red bicolor, ms | T. erecta | 1653 | white | 8191-14 | semi-dwarf, white |
| Z. elegans | 78-11 | gold-red bicolor, ms | T. erecta | 1653 | white | 8191-15 | semi-dwarf, white |

TABLE 1-continued

| Female parent genus species | Female parent name | Description of female parent | Male parent genus species | Male parent name | Description of male parent | Intergeneric hybrid name | Description of intergeneric hybrid |
|---|---|---|---|---|---|---|---|
| Z. elegans | 78-11 | gold-red bicolor, ms | T. erecta | 1653 | white | 8191-16 | semi-dwarf, white |
| Z. elegans | 78-11 | gold-red bicolor, ms | T. erecta | 1653 | white | 8191-17 | semi-dwarf, white |
| Z. elegans | 78-11 | gold-red bicolor, ms | T. erecta | 1653 | white | 8191-18 | semi-dwarf, white |
| Z. elegans | 78-11 | gold-red bicolor, ms | T. erecta | 1653 | white | 8191-19 | semi-dwarf, white |
| Z. elegans | 78-11 | gold-red bicolor, ms | T. erecta | 1653 | white | 8191-20 | semi-dwarf, white |
| Z. elegans | 78-11 | gold-red bicolor, ms | T. erecta | 1653 | white | 8191-21 | semi-dwarf, white |
| Z. elegans | 78-11 | gold-red bicolor, ms | T. erecta | 1653 | white | 8191-22 | semi-dwarf, white |
| Z. elegans | 78-11 | gold-red bicolor, ms | T. erecta | 1653 | white | 8191-23 | semi-dwarf, white |
| Z. elegans | 78-11 | gold-red bicolor, ms | T. erecta | 1653 | white | 8191-24 | semi-dwarf, white |
| Z. elegans | 78-11 | gold-red bicolor, ms | T. erecta | 1653 | white | 8191-25 | semi-dwarf, white |
| Z. elegans | 78-11 | gold-red bicolor, ms | T. erecta | 1653 | white | 8191-26 | semi-dwarf, white |
| Z. elegans | 78-11 | gold-red bicolor, ms | T. erecta | 1653 | white | 8191-27 | semi-dwarf, white |
| Z. elegans | 78-11 | gold-red bicolor, ms | T. erecta | 1653 | white | 8191-28 | semi-dwarf, white |
| Z. elegans | 78-11 | gold-red bicolor, ms | T. erecta | 1653 | white | 8191-29 | semi-dwarf, white |
| Z. elegans | 78-11 | gold-red bicolor, ms | T. erecta | 1653 | white | 8191-30 | semi-dwarf, white |
| Z. elegans | 78-11 | gold-red bicolor, ms | T. erecta | 1653 | white | 8191-31 | semi-dwarf, white |
| Z. elegans | 78-11 | gold-red bicolor, ms | T. erecta | 1653 | white | 8191-32 | semi-dwarf, white |
| Z. elegans | 78-11 | gold-red bicolor, ms | T. erecta | 1653 | white | 8191-33 | semi-dwarf, white |
| Z. elegans | 78-11 | gold-red bicolor, ms | T. erecta | 1653 | white | 8191-34 | semi-dwarf, orange |
| Z. elegans | 78-11 | gold-red bicolor, ms | T. erecta | 1653 | white | 8191-35 | semi-dwarf, yellow |
| Z. elegans | 78-11 | gold-red bicolor, ms | T. erecta | 1653 | white | 8191-36 | semi-dwarf, yellow |
| Z. elegans | 78-11 | gold-red bicolor, ms | T. erecta | 1653 | white | 8191-37 | semi-dwarf, yellow |
| Z. elegans | 78-11 | gold-red bicolor, ms | T. erecta | 1653 | white | 8191-38 | semi-dwarf, yellow |
| Z. elegans | 78-11 | gold-red bicolor, ms | T. erecta | 1653 | white | 8191-39 | semi-dwarf, yellow |
| Z. elegans | 78-11 | gold-red bicolor, ms | T. erecta | 1653 | white | 8191-40 | dwarf, ms |
| Z. elegans | 78-11 | gold-red bicolor, ms | T. erecta | 1653 m | white | 8191-41 | dwarf, ms |
| Z. elegans | 78-11 | gold-red bicolor, ms | T. erecta | 1653 m | white | 8191-42 | dwarf, ms |
| Z. elegans | 78-11 | gold-red bicolor, ms | T. erecta | 1653 m | white | 8191-43 | dwarf, ms |
| Z. elegans | 78-11 | gold-red bicolor, ms | T. erecta | 1653 m | white | 8191-44 | dwarf, ms |
| Z. elegans | 78-11 | gold-red bicolor, ms | T. erecta | 1653 m | white | 8191-45 | dwarf, ms |
| Z. elegans | 78-11 | gold-red bicolor, ms | T. erecta | 1653 m | white | 8191-46 | dwarf, ms |
| Z. elegans | 78-11 | gold-red bicolor, ms | T. erecta | 1653 m | white | 8191-47 | dwarf, ms |
| Z. elegans | 78-11 | gold-red bicolor, ms | T. erecta | 1653 m | white | 8191-48 | tall, white |
| Z. elegans | 78-11 | gold-red bicolor, ms | T. erecta | 1653 m | white | 8191-49 | tall, white |
| Z. elegans | 78-11 | gold-red bicolor, ms | T. erecta | 1653 m | white | 8191-50 | tall, white |
| Z. elegans | 78-11 | gold-red bicolor, ms | T. erecta | 1653 m | white | 8191-51 | tall, white |
| Z. elegans | 78-11 | gold-red bicolor, ms | T. erecta | 1653 m | white | 8191-52 | tall, white |

TABLE 1-continued

| Female parent genus species | Female parent name | Description of female parent | Male parent genus species | Male parent name | Description of male parent | Intergeneric hybrid name | Description of intergeneric hybrid |
|---|---|---|---|---|---|---|---|
| Z. elegans | 78-11 | gold-red bicolor, ms | T. erecta | 1653 m | white | 8191-53 | tall, white |
| Z. elegans | 78-11 | gold-red bicolor, ms | T. erecta | 1653 m | white | 8191-54 | tall, white |
| Z. elegans | 78-11 | gold-red bicolor, ms | T. erecta | 1653 m | white | 8191-55 | tall, white |
| Z. elegans | 78-11 | gold-red bicolor, ms | T. erecta | 1653 m | white | 8191-56 | tall, white |
| Z. elegans | 78-11 | gold-red bicolor, ms | T. erecta | 1653 m | white | 8191-57 | tall, white |
| Z. elegans | 78-11 | gold-red bicolor, ms | T. erecta | 1653 m | white | 8191-58 | tall, white |
| Z. elegans | 78-11 | gold-red bicolor, ms | T. erecta | 1653 m | white | 8191-59 | tall, yellow |
| Z. elegans | 78-11 | gold-red bicolor, ms | T. erecta | 1653 m | white | 8191-60 | tall, yellow |
| Z. elegans | 78-13 | gold-red bicolor, ms | T. erecta | 1653 m | white | 8192-1 | dwarf, rose |
| Z. elegans | 78-13 | gold-red bicolor, ms | T. erecta | 1653 m | white | 8192-2 | dwarf, rose |
| Z. elegans | 78-13 | gold-red bicolor, ms | T. erecta | 1653 m | white | 8192-3 | dwarf, rose |
| Z. elegans | 78-13 | gold-red bicolor, ms | T. erecta | 1653 m | white | 8192-4 | dwarf, rose |
| Z. elegans | 78-13 | gold-red bicolor, ms | T. erecta | 1653 m | white | 8192-5 | dwarf, rose |
| Z. elegans | 78-13 | gold-red bicolor, ms | T. erecta | 1653 m | white | 8192-6 | semi-dwarf, ms |
| Z. elegans | 78-13 | gold-red bicolor, ms | T. erecta | 1653 m | white | 8192-7 | semi-dwarf, rose |
| Z. elegans | 78-13 | gold-red bicolor, ms | T. erecta | 1653 m | white | 8192-8 | semi-dwarf, rose |
| Z. elegans | 78-13 | gold-red bicolor, ms | T. erecta | 1653 m | white | 8192-9 | semi-dwarf, rose |
| Z. elegans | 78-13 | gold-red bicolor, ms | T. erecta | 1653 m | white | 8192-10 | semi-dwarf, rose |
| Z. elegans | 78-13 | gold-red bicolor, ms | T. erecta | 1653 m | white | 8192-11 | semi-dwarf, rose |
| Z. elegans | 78-13 | gold-red bicolor, ms | T. erecta | 1653 m | white | 8192-12 | semi-dwarf, rose |
| Z. elegans | 78-13 | gold-red bicolor, ms | T. erecta | 1653 m | white | 8192-13 | semi-dwarf, rose |
| Z. elegans | 78-13 | gold-red bicolor, ms | T. erecta | 1653 m | white | 8192-14 | semi-dwarf, rose |
| Z. elegans | 78-13 | gold-red bicolor, ms | T. erecta | 1653 m | white | 8192-15 | semi-dwarf, rose |
| Z. elegans | 78-13 | gold-red bicolor, ms | T. erecta | 1653 m | white | 8192-16 | tall, rose |
| Z. elegans | 78-13 | gold-red bicolor, ms | T. erecta | 1653 m | white | 8192-17 | tall, rose |
| Z. elegans | 79-3 | gold-red bicolor, ms | T. erecta | 1653 m | white | 8193-1 | dwarf, cream |
| Z. elegans | 79-3 | gold-red bicolor, ms | T. erecta | 1653 m | white | 8193-2 | dwarf, cream |
| Z. elegans | 79-3 | gold-red bicolor, ms | T. erecta | 1653 m | white | 8193-3 | dwarf, cream |
| Z. elegans | 79-3 | gold-red bicolor, ms | T. erecta | 1653 m | white | 8193-4 | dwarf, yellow |
| Z. elegans | 79-3 | gold-red bicolor, ms | T. erecta | 1653 m | white | 8193-5 | dwarf, yellow |
| Z. elegans | 79-3 | gold-red bicolor, ms | T. erecta | 1653 m | white | 8193-6 | dwarf, yellow |
| Z. elegans | 79-3 | gold-red bicolor, ms | T. erecta | 1653 m | white | 8193-7 | dwarf, yellow |
| Z. elegans | 79-3 | gold-red bicolor, ms | T. erecta | 1653 m | white | 8193-8 | dwarf, yellow |
| Z. elegans | 79-3 | gold-red bicolor, ms | T. erecta | 1653 m | white | 8193-9 | dwarf, yellow |
| Z. elegans | 79-3 | gold-red bicolor, ms | T. erecta | 1653 m | white | 8193-10 | dwarf, yellow |
| Z. elegans | 79-3 | gold-red bicolor, ms | T. erecta | 1653 m | white | 8193-11 | dwarf, yellow |
| Z. elegans | 79-3 | gold-red bicolor, ms | T. erecta | 1653 m | white | 8193-12 | dwarf, yellow |

TABLE 1-continued

| Female parent genus species | Female parent name | Description of female parent | Male parent genus species | Male parent name | Description of male parent | Intergeneric hybrid name | Description of intergeneric hybrid |
|---|---|---|---|---|---|---|---|
| Z. elegans | 79-3 | gold-red bicolor, ms | T. erecta | 1653 m | white | 8193-13 | dwarf, yellow |
| Z. elegans | 79-3 | gold-red bicolor, ms | T. erecta | 1653 m | white | 8193-14 | dwarf, yellow |
| Z. elegans | 79-3 | gold-red bicolor, ms | T. erecta | 1653 m | white | 8193-15 | dwarf, yellow |
| Z. elegans | 79-3 | gold-red bicolor, ms | T. erecta | 1653 m | white | 8193-16 | dwarf, yellow |
| Z. elegans | 79-3 | gold-red bicolor, ms | T. erecta | 1653 m | white | 8193-17 | dwarf, yellow |
| Z. elegans | 79-3 | gold-red bicolor, ms | T. erecta | 1653 m | white | 8193-18 | dwarf, yellow |
| Z. elegans | 79-3 | gold-red bicolor, ms | T. erecta | 1653 m | white | 8193-19 | dwarf, yellow |
| Z. elegans | 79-3 | gold-red bicolor, ms | T. erecta | 1653 m | white | 8193-20 | dwarf, yellow |
| Z. elegans | 79-3 | gold-red bicolor, ms | T. erecta | 1653 m | white | 8193-21 | ms, tall |
| Z. elegans | 79-3 | gold-red bicolor, ms | T. erecta | 1653 m | white | 8193-22 | tall, yellow |
| Z. elegans | 79-3 | gold-red bicolor, ms | T. erecta | 1653 m | white | 8193-23 | tall, yellow |
| Z. elegans | 79-3 | gold-red bicolor, ms | T. erecta | 1653 m | white | 8193-24 | tall, yellow |
| Z. elegans | 79-3 | gold-red bicolor, ms | T. erecta | 1653 m | white | 8193-25 | tall, yellow |
| Z. elegans | 79-3 | gold-red bicolor, ms | T. erecta | 1653 m | white | 8193-26 | tall, yellow |
| Z. elegans | 79-3 | gold-red bicolor, ms | T. erecta | 1653 m | white | 8193-27 | tall, yellow |
| Z. elegans | 79-3 | gold-red bicolor, ms | T. erecta | 1653 m | white | 8193-28 | tall, yellow |
| Z. elegans | 79-3 | gold-red bicolor, ms | T. erecta | 1653 m | white | 8193-29 | tall, yellow |
| Z. elegans | 78-14 | gold-red bicolor, ms | T. erecta | 1653 m | white | 8194-1 | dwarf, white |
| Z. elegans | 78-14 | gold-red bicolor, ms | T. erecta | 1653 m | white | 8194-2 | dwarf, white |
| Z. elegans | 78-14 | gold-red bicolor, ms | T. erecta | 1653 m | white | 8194-3 | dwarf, white |
| Z. elegans | 78-14 | gold-red bicolor, ms | T. erecta | 1653 m | white | 8194-4 | dwarf, white |
| Z. elegans | 78-14 | gold-red bicolor, ms | T. erecta | 1653 m | white | 8194-5 | dwarf, white |
| Z. elegans | 78-14 | gold-red bicolor, ms | T. erecta | 1653 m | white | 8194-6 | dwarf, white |
| Z. elegans | 78-14 | gold-red bicolor, ms | T. erecta | 1653 m | white | 8194-7 | dwarf, white |
| Z. elegans | 78-14 | gold-red bicolor, ms | T. erecta | 1653 m | white | 8194-8 | dwarf, ms |
| Z. elegans | 78-14 | gold-red bicolor, ms | T. erecta | 1653 m | white | 8194-9 | dwarf, ms |
| Z. elegans | 78-14 | gold-red bicolor, ms | T. erecta | 1653 m | white | 8194-10 | dwarf, ms |
| Z. elegans | 78-14 | gold-red bicolor, ms | T. erecta | 1653 m | white | 8194-11 | dwarf, ms |
| Z. elegans | 78-14 | gold-red bicolor, ms | T. erecta | 1653 m | white | 8194-12 | semi-dwarf, white |
| Z. elegans | 78-14 | gold-red bicolor, ms | T. erecta | 1653 m | white | 8194-13 | semi-dwarf, white |
| Z. elegans | 78-14 | gold-red bicolor, ms | T. erecta | 1653 m | white | 8194-14 | semi-dwarf, white |
| Z. elegans | 78-14 | gold-red bicolor, ms | T. erecta | 1653 m | white | 8194-15 | semi-dwarf, white |
| Z. elegans | 78-14 | gold-red bicolor, ms | T. erecta | 1653 m | white | 8194-16 | semi-dwarf, white |
| Z. elegans | 78-14 | gold-red bicolor, ms | T. erecta | 1653 m | white | 8194-17 | semi-dwarf, white |
| Z. elegans | 78-14 | gold-red bicolor, ms | T. erecta | 1653 m | white | 8194-18 | semi-dwarf, white |
| Z. elegans | 78-14 | gold-red bicolor, ms | T. erecta | 1653 m | white | 8194-19 | semi-dwarf, white |
| Z. elegans | 78-14 | gold-red bicolor, ms | T. erecta | 1653 m | white | 8194-20 | semi-dwarf, white |

TABLE 1-continued

| Female parent genus species | Female parent name | Description of female parent | Male parent genus species | Male parent name | Description of male parent | Intergeneric hybrid name | Description of intergeneric hybrid |
|---|---|---|---|---|---|---|---|
| Z. elegans | 78-14 | gold-red bicolor, ms | T. erecta | 1653 m | white | 8194-21 | semi-dwarf, white |
| Z. elegans | 78-14 | gold-red bicolor, ms | T. erecta | 1653 m | white | 8194-22 | semi-dwarf, white |
| Z. elegans | 78-14 | gold-red bicolor, ms | T. erecta | 1653 m | white | 8194-23 | semi-dwarf, white |
| Z. elegans | 78-14 | gold-red bicolor, ms | T. erecta | 1653 m | white | 8194-24 | tall, ms |
| Z. elegans | 78-14 | gold-red bicolor, ms | T. erecta | 1653 m | white | 8194-25 | tall, ms |
| Z. elegans | 78-14 | gold-red bicolor, ms | T. erecta | 1653 m | white | 8194-26 | tall, ms |
| Z. elegans | 78-14 | gold-red bicolor, ms | T. erecta | 1653 m | white | 8194-27 | tall, yellow |
| Z. elegans | 78-14 | gold-red bicolor, ms | T. erecta | 1653 m | white | 8194-28 | tall, yellow |
| Z. elegans | 78-14 | gold-red bicolor, ms | T. erecta | 1653 m | white | 8194-29 | tall, white |
| Z. elegans | 78-14 | gold-red bicolor, ms | T. erecta | 1653 m | white | 8194-30 | tall, white |
| Z. elegans | 78-14 | gold-red bicolor, ms | T. erecta | 1653 m | white | 8194-31 | tall, white |
| Z. elegans | 78-14 | gold-red bicolor, ms | T. erecta | 1653 m | white | 8194-32 | tall, white |
| Z. elegans | 78-14 | gold-red bicolor, ms | T. erecta | 1653 m | white | 8194-33 | tall, white |
| Z. elegans | 78-14 | gold-red bicolor, ms | T. erecta | 1653 m | white | 8194-34 | tall, white |
| Z. elegans | 82-3 | gold-red bicolor, ms | T. erecta | 1653 m | white | 8195-1 | semi-dwarf, ms |
| Z. elegans | 82-3 | gold-red bicolor, ms | T. erecta | 1653 m | white | 8195-2 | semi-dwarf, ms |
| Z. elegans | 82-3 | gold-red bicolor, ms | T. erecta | 1653 m | white | 8195-3 | semi-dwarf, ms |
| Z. elegans | 82-3 | gold-red bicolor, ms | T. erecta | 1653 m | white | 8195-4 | semi-dwarf, ms |
| Z. elegans | 82-3 | gold-red bicolor, ms | T. erecta | 1653 m | white | 8195-5 | semi-dwarf, ms |
| Z. elegans | 82-3 | gold-red bicolor, ms | T. erecta | 1653 m | white | 8195-6 | semi-dwarf, vase shape, branched, yellow |
| Z. elegans | 82-3 | gold-red bicolor, ms | T. erecta | 1653 m | white | 8195-7 | semi-dwarf, vase shape, branched, yellow |
| Z. elegans | 82-3 | gold-red bicolor, ms | T. erecta | 1653 m | white | 8195-8 | semi-dwarf, vase shape, branched, yellow |
| Z. elegans | 82-3 | gold-red bicolor, ms | T. erecta | 1653 m | white | 8195-9 | semi-dwarf, vase shape, branched, yellow |
| Z. elegans | 82-3 | gold-red bicolor, ms | T. erecta | 1653 m | white | 8195-10 | semi-dwarf, vase shape, branched, yellow |
| Z. elegans | 82-3 | gold-red bicolor, ms | T. erecta | 1653 m | white | 8195-11 | semi-dwarf, vase shape, branched, yellow |
| Z. elegans | 82-3 | gold-red bicolor, ms | T. erecta | 1653 m | white | 8195-12 | semi-dwarf, vase shape, branched, yellow |
| Z. elegans | 82-3 | gold-red bicolor, ms | T. erecta | 1653 m | white | 8195-13 | semi-dwarf, vase shape, branched, yellow |
| Z. elegans | 82-3 | gold-red bicolor, ms | T. erecta | 1653 m | white | 8195-14 | semi-dwarf, vase shape, branched, yellow |

TABLE 1-continued

| Female parent genus species | Female parent name | Description of female parent | Male parent genus species | Male parent name | Description of male parent | Intergeneric hybrid name | Description of intergeneric hybrid |
|---|---|---|---|---|---|---|---|
| Z. elegans | 82-3 | gold-red bicolor, ms | T. erecta | 1653 m | white | 8195-15 | semi-dwarf, vase shape, branched, yellow |
| Z. elegans | 82-3 | gold-red bicolor, ms | T. erecta | 1653 m | white | 8195-16 | semi-dwarf, yellow |
| Z. elegans | 82-3 | gold-red bicolor, ms | T. erecta | 1653 m | white | 8195-17 | semi-dwarf, yellow |
| Z. elegans | 82-3 | gold-red bicolor, ms | T. erecta | 1653 m | white | 8195-18 | semi-dwarf, yellow |
| Z. elegans | 82-3 | gold-red bicolor, ms | T. erecta | 1653 m | white | 8195-19 | semi-dwarf, yellow |
| Z. elegans | 82-3 | gold-red bicolor, ms | T. erecta | 1653 m | white | 8195-20 | semi-dwarf, yellow |
| Z. elegans | 82-3 | gold-red bicolor, ms | T. erecta | 1653 m | white | 8195-21 | semi-dwarf, yellow |
| Z. elegans | 82-3 | gold-red bicolor, ms | T. erecta | 1653 m | white | 8195-22 | semi-dwarf, yellow |
| Z. elegans | 82-3 | gold-red bicolor, ms | T. erecta | 1653 m | white | 8195-23 | semi-dwarf, yellow |
| Z. elegans | 82-3 | gold-red bicolor, ms | T. erecta | 1653 m | white | 8195-24 | semi-dwarf, yellow |
| Z. elegans | 82-3 | gold-red bicolor, ms | T. erecta | 1653 m | white | 8195-25 | semi-dwarf, yellow |
| Z. elegans | 82-3 | gold-red bicolor, ms | T. erecta | 1653 m | white | 8195-26 | semi-dwarf, yellow |
| Z. elegans | 82-3 | gold-red bicolor, ms | T. erecta | 1653 m | white | 8195-27 | semi-dwarf, yellow |
| Z. elegans | 82-3 | gold-red bicolor, ms | T. erecta | 1653 m | white | 8195-28 | semi-dwarf, yellow |
| Z. elegans | 82-3 | gold-red bicolor, ms | T. erecta | 1653 m | white | 8195-29 | semi-dwarf, yellow |
| Z. elegans | 82-3 | gold-red bicolor, ms | T. erecta | 1653 m | white | 8195-30 | semi-dwarf, yellow |
| Z. elegans | 82-3 | gold-red bicolor, ms | T. erecta | 1653 m | white | 8195-31 | semi-dwarf, yellow |
| Z. elegans | 82-3 | gold-red bicolor, ms | T. erecta | 1653 m | white | 8195-32 | semi-dwarf, yellow |
| Z. elegans | 80-10 | gold-red bicolor, ms | T. erecta | 1653 m | white | 8196-1 | dwarf, ms |
| Z. elegans | 80-10 | gold-red bicolor, ms | T. erecta | 1653 m | white | 8196-2 | dwarf, ms |
| Z. elegans | 80-10 | gold-red bicolor, ms | T. erecta | 1653 m | white | 8196-3 | dwarf, ms |
| Z. elegans | 80-10 | gold-red bicolor, ms | T. erecta | 1653 m | white | 8196-4 | dwarf, ms |
| Z. elegans | 80-10 | gold-red bicolor, ms | T. erecta | 1653 m | white | 8196-5 | dwarf, ms |
| Z. elegans | 80-10 | gold-red bicolor, ms | T. erecta | 1653 m | white | 8196-6 | dwarf, ms |
| Z. elegans | 80-10 | gold-red bicolor, ms | T. erecta | 1653 m | white | 8196-7 | dwarf, ms |
| Z. elegans | 80-10 | gold-red bicolor, ms | T. erecta | 1653 m | white | 8196-8 | dwarf, ms |
| Z. elegans | 80-10 | gold-red bicolor, ms | T. erecta | 1653 m | white | 8196-9 | dwarf, ms |
| Z. elegans | 80-10 | gold-red bicolor, ms | T. erecta | 1653 m | white | 8196-10 | dwarf, ms |
| Z. elegans | 80-10 | gold-red bicolor, ms | T. erecta | 1653 m | white | 8196-11 | dwarf, ms |
| Z. elegans | 80-10 | gold-red bicolor, ms | T. erecta | 1653 m | white | 8196-12 | dwarf, ms |
| Z. elegans | 80-10 | gold-red bicolor, ms | T. erecta | 1653 m | white | 8196-13 | dwarf, ms |
| Z. elegans | 80-10 | gold-red bicolor, ms | T. erecta | 1653 m | white | 8196-14 | dwarf, ms |
| Z. elegans | 80-10 | gold-red bicolor, ms | T. erecta | 1653 m | white | 8196-15 | dwarf, coral orange |
| Z. elegans | 80-10 | gold-red bicolor, ms | T. erecta | 1653 m | white | 8196-16 | dwarf, coral orange |
| Z. elegans | 80-10 | gold-red bicolor, ms | T. erecta | 1653 m | white | 8196-17 | dwarf, coral orange |
| Z. elegans | 80-10 | gold-red bicolor, ms | T. erecta | 1653 m | white | 8196-18 | dwarf, coral orange |

TABLE 1-continued

| Female parent genus species | Female parent name | Description of female parent | Male parent genus species | Male parent name | Description of male parent | Intergeneric hybrid name | Description of intergeneric hybrid |
|---|---|---|---|---|---|---|---|
| Z. elegans | 80-10 | gold-red bicolor, ms | T. erecta | 1653 m | white | 8196-19 | dwarf, coral orange |
| Z. elegans | 80-10 | gold-red bicolor, ms | T. erecta | 1653 m | white | 8196-20 | dwarf, coral orange |
| Z. elegans | 80-10 | gold-red bicolor, ms | T. erecta | 1653 m | white | 8196-21 | dwarf, coral orange |
| Z. elegans | 80-10 | gold-red bicolor, ms | T. erecta | 1653 m | white | 8196-22 | dwarf, coral orange |
| Z. elegans | 80-10 | gold-red bicolor, ms | T. erecta | 1653 m | white | 8196-23 | dwarf, coral orange |
| Z. elegans | 80-10 | gold-red bicolor, ms | T. erecta | 1653 m | white | 8196-24 | dwarf, coral orange |
| Z. elegans | 80-10 | gold-red bicolor, ms | T. erecta | 1653 m | white | 8196-25 | dwarf, coral orange |
| Z. elegans | 80-10 | gold-red bicolor, ms | T. erecta | 1653 m | white | 8196-26 | dwarf, coral orange |
| Z. elegans | 80-10 | gold-red bicolor, ms | T. erecta | 1653 m | white | 8196-27 | dwarf, coral orange |
| Z. elegans | 80-10 | gold-red bicolor, ms | T. erecta | 1653 m | white | 8196-28 | dwarf, pink |
| Z. elegans | 80-10 | gold-red bicolor, ms | T. erecta | 1653 m | white | 8196-29 | dwarf, pink |
| Z. elegans | 80-10 | gold-red bicolor, ms | T. erecta | 1653 m | white | 8196-30 | dwarf, pink |
| Z. elegans | 80-10 | gold-red bicolor, ms | T. erecta | 1653 m | white | 8196-31 | dwarf, pink |
| Z. elegans | 80-10 | gold-red bicolor, ms | T. erecta | 1653 m | white | 8196-32 | dwarf, pink |
| Z. elegans | 80-10 | gold-red bicolor, ms | T. erecta | 1653 m | white | 8196-33 | dwarf, pink |
| Z. elegans | 80-10 | gold-red bicolor, ms | T. erecta | 1653 m | white | 8196-34 | dwarf, pink |
| Z. elegans | 80-10 | gold-red bicolor, ms | T. erecta | 1653 m | white | 8196-35 | dwarf, pink |
| Z. elegans | 80-10 | gold-red bicolor, ms | T. erecta | 1653 m | white | 8196-36 | dwarf, pink |
| Z. elegans | 80-10 | gold-red bicolor, ms | T. erecta | 1653 m | white | 8196-37 | dwarf, pink |
| Z. elegans | 80-10 | gold-red bicolor, ms | T. erecta | 1653 m | white | 8196-38 | dwarf, pink |
| Z. elegans | 80-10 | gold-red bicolor, ms | T. erecta | 1653 m | white | 8196-39 | dwarf, pink |
| Z. elegans | 80-10 | gold-red bicolor, ms | T. erecta | 1653 m | white | 8196-40 | dwarf, pink |
| Z. elegans | 80-10 | gold-red bicolor, ms | T. erecta | 1653 m | white | 8196-41 | dwarf, pink |
| Z. elegans | 80-10 | gold-red bicolor, ms | T. erecta | 1653 m | white | 8196-42 | dwarf, pink |
| Z. elegans | 80-10 | gold-red bicolor, ms | T. erecta | 1653 m | white | 8196-43 | dwarf, pink |
| Z. elegans | 80-10 | gold-red bicolor, ms | T. erecta | 1653 m | white | 8196-44 | dwarf, pink |
| Z. elegans | 80-10 | gold-red bicolor, ms | T. erecta | 1653 m | white | 8196-45 | dwarf, pink |

As shown in Table 1, numerous intergeneric hybrid plants of Z. elegans and T. erecta have been produced by the method of the invention, with assorted flower colors, plant sizes and sterility. Table 1 also shows unexpected new flower colors and plant habits present in the intergeneric hybrids that were not present in either parent species of Z. elegans or T. erecta alone. For example, intergeneric hybrids 8193-1, 8193-2 and 8193-3 had a cream flower color, which is a new and different flower color not seen in Z. elegans. Additionally, intergeneric hybrid plants 8195-6, 8195-7, 8195-8, 8195-9, 8195-10, 8195-11, 8195-12, 8195-13, 8195-14 and 8195-15 all surprisingly had a vase shaped and branched plant habit, which is a new and different plant habit not seen in Z. elegans or T. erecta. Many more intergeneric hybrid plants of Z. elegans and T. erecta have been produced than are shown in Table 1.

Table 2 shows a comparison of the powdery mildew expression of the intergeneric hybrid plants of Z. elegans and T. erecta produced by the method of the invention and listed in Table 1, as compared to the powdery mildew expression of straight genera of Z. elegans or T. erecta to demonstrate the improved powdery mildew resistance of the intergeneric hybrid plants produced. Data was taken in 2014. Column 1 shows the genus and species, column 2 shows the name, column 3 shows the brief description and column 4 shows the powdery mildew expression. In Table 2, m indicates that a mass of plants was made for pollination and harvest of seed, ms indicates male sterile, and an asterisk (*) indicates that the line will segregate for the male sterile (ms) condition. When a color is listed, it indicates the flower color. Powdery mildew expression is scored from 1 to 5, where 1 indicates high mildew expression and 5 indicates the least mildew expression.

TABLE 2

| Genus species | Name | Description | Powdery mildew expression (1 high mildew - 5 least mildew) |
|---|---|---|---|
| Intergeneric hybrid of Z. elegans and T. erecta | 8191-1 | dwarf, white | 5 |
| Intergeneric hybrid of Z. elegans and T. erecta | 8191-2 | dwarf, white | 5 |
| Intergeneric hybrid of Z. elegans and T. erecta | 8191-3 | dwarf, white | 5 |
| Intergeneric hybrid of Z. elegans and T. erecta | 8191-4 | dwarf, white | 5 |
| Intergeneric hybrid of Z. elegans and T. erecta | 8191-5 | dwarf, white | 5 |
| Intergeneric hybrid of Z. elegans and T. erecta | 8191-6 | dwarf, white | 5 |
| Intergeneric hybrid of Z. elegans and T. erecta | 8191-7 | dwarf, white | 5 |
| Intergeneric hybrid of Z. elegans and T. erecta | 8191-8 | dwarf, white | 5 |
| Intergeneric hybrid of Z. elegans and T. erecta | 8191-9 | dwarf, white | 5 |
| Intergeneric hybrid of Z. elegans and T. erecta | 8191-10 | semi-dwarf, white | 5 |
| Intergeneric hybrid of Z. elegans and T. erecta | 8191-11 | semi-dwarf, white | 5 |
| Intergeneric hybrid of Z. elegans and T. erecta | 8191-12 | semi-dwarf, white | 5 |
| Intergeneric hybrid of Z. elegans and T. erecta | 8191-13 | semi-dwarf, white | 5 |
| Intergeneric hybrid of Z. elegans and T. erecta | 8191-14 | semi-dwarf, white | 5 |
| Intergeneric hybrid of Z. elegans and T. erecta | 8191-15 | semi-dwarf, white | 5 |
| Intergeneric hybrid of Z. elegans and T. erecta | 8191-16 | semi-dwarf, white | 5 |
| Intergeneric hybrid of Z. elegans and T. erecta | 8191-17 | semi-dwarf, white | 5 |
| Intergeneric hybrid of Z. elegans and T. erecta | 8191-18 | semi-dwarf, white | 5 |
| Intergeneric hybrid of Z. elegans and T. erecta | 8191-19 | semi-dwarf, white | 5 |
| Intergeneric hybrid of Z. elegans and T. erecta | 8191-20 | semi-dwarf, white | 5 |
| Intergeneric hybrid of Z. elegans and T. erecta | 8191-21 | semi-dwarf, white | 5 |
| Intergeneric hybrid of Z. elegans and T. erecta | 8191-22 | semi-dwarf, white | 5 |
| Intergeneric hybrid of Z. elegans and T. erecta | 8191-23 | semi-dwarf, white | 5 |
| Intergeneric hybrid of Z. elegans and T. erecta | 8191-24 | semi-dwarf, white | 5 |
| Intergeneric hybrid of Z. elegans and T. erecta | 8191-25 | semi-dwarf, white | 5 |
| Intergeneric hybrid of Z. elegans and T. erecta | 8191-26 | semi-dwarf, white | 5 |
| Intergeneric hybrid of Z. elegans and T. erecta | 8191-27 | semi-dwarf, white | 5 |
| Intergeneric hybrid of Z. elegans and T. erecta | 8191-28 | semi-dwarf, white | 5 |
| Intergeneric hybrid of Z. elegans and T. erecta | 8191-29 | semi-dwarf, white | 5 |
| Intergeneric hybrid of Z. elegans and T. erecta | 8191-30 | semi-dwarf, white | 5 |
| Intergeneric hybrid of Z. elegans and T. erecta | 8191-31 | semi-dwarf, white | 5 |
| Intergeneric hybrid of Z. elegans and T. erecta | 8191-32 | semi-dwarf, white | 5 |
| Intergeneric hybrid of Z. elegans and T. erecta | 8191-33 | semi-dwarf, white | 5 |
| Intergeneric hybrid of Z. elegans and T. erecta | 8191-34 | semi-dwarf, orange | 5 |
| Intergeneric hybrid of Z. elegans and T. erecta | 8191-35 | semi-dwarf, yellow | 5 |
| Intergeneric hybrid of Z. elegans and T. erecta | 8191-36 | semi-dwarf, yellow | 5 |
| Intergeneric hybrid of Z. elegans and T. erecta | 8191-37 | semi-dwarf, yellow | 5 |
| Intergeneric hybrid of Z. elegans and T. erecta | 8191-38 | semi-dwarf, yellow | 5 |
| Intergeneric hybrid of Z. elegans and T. erecta | 8191-39 | semi-dwarf, yellow | 5 |
| Intergeneric hybrid of Z. elegans and T. erecta | 8191-40 | dwarf, ms | 5 |
| Intergeneric hybrid of Z. elegans and T. erecta | 8191-41 | dwarf, ms | 5 |
| Intergeneric hybrid of Z. elegans and T. erecta | 8191-42 | dwarf, ms | 5 |
| Intergeneric hybrid of Z. elegans and T. erecta | 8191-43 | dwarf, ms | 5 |
| Intergeneric hybrid of Z. elegans and T. erecta | 8191-44 | dwarf, ms | 5 |
| Intergeneric hybrid of Z. elegans and T. erecta | 8191-45 | dwarf, ms | 5 |
| Intergeneric hybrid of Z. elegans and T. erecta | 8191-46 | dwarf, ms | 5 |
| Intergeneric hybrid of Z. elegans and T. erecta | 8191-47 | dwarf, ms | 5 |
| Intergeneric hybrid of Z. elegans and T. erecta | 8191-48 | tall, white | 5 |
| Intergeneric hybrid of Z. elegans and T. erecta | 8191-49 | tall, white | 5 |
| Intergeneric hybrid of Z. elegans and T. erecta | 8191-50 | tall, white | 5 |
| Intergeneric hybrid of Z. elegans and T. erecta | 8191-51 | tall, white | 5 |
| Intergeneric hybrid of Z. elegans and T. erecta | 8191-52 | tall, white | 5 |
| Intergeneric hybrid of Z. elegans and T. erecta | 8191-53 | tall, white | 5 |
| Intergeneric hybrid of Z. elegans and T. erecta | 8191-54 | tall, white | 5 |
| Intergeneric hybrid of Z. elegans and T. erecta | 8191-55 | tall, white | 5 |
| Intergeneric hybrid of Z. elegans and T. erecta | 8191-56 | tall, white | 5 |
| Intergeneric hybrid of Z. elegans and T. erecta | 8191-57 | tall, white | 5 |
| Intergeneric hybrid of Z. elegans and T. erecta | 8191-58 | tall, white | 5 |
| Intergeneric hybrid of Z. elegans and T. erecta | 8191-59 | tall, yellow | 5 |
| Intergeneric hybrid of Z. elegans and T. erecta | 8191-60 | tall, yellow | 5 |
| Intergeneric hybrid of Z. elegans and T. erecta | 8192-1 | dwarf, rose | 3.5 |
| Intergeneric hybrid of Z. elegans and T. erecta | 8192-2 | dwarf, rose | 3.5 |
| Intergeneric hybrid of Z. elegans and T. erecta | 8192-3 | dwarf, rose | 3.5 |
| Intergeneric hybrid of Z. elegans and T. erecta | 8192-4 | dwarf, rose | 3.5 |
| Intergeneric hybrid of Z. elegans and T. erecta | 8192-5 | dwarf, rose | 3.5 |
| Intergeneric hybrid of Z. elegans and T. erecta | 8192-6 | semi-dwarf, ms | 3.5 |
| Intergeneric hybrid of Z. elegans and T. erecta | 8192-7 | semi-dwarf, rose | 3.5 |
| Intergeneric hybrid of Z. elegans and T. erecta | 8192-8 | semi-dwarf, rose | 3.5 |
| Intergeneric hybrid of Z. elegans and T. erecta | 8192-9 | semi-dwarf, rose | 3.5 |
| Intergeneric hybrid of Z. elegans and T. erecta | 8192-10 | semi-dwarf, rose | 3.5 |

TABLE 2-continued

| Genus species | Name | Description | Powdery mildew expression (1 high mildew - 5 least mildew) |
|---|---|---|---|
| Intergeneric hybrid of Z. elegans and T. erecta | 8192-11 | semi-dwarf, rose | 3.5 |
| Intergeneric hybrid of Z. elegans and T. erecta | 8192-12 | semi-dwarf, rose | 3.5 |
| Intergeneric hybrid of Z. elegans and T. erecta | 8192-13 | semi-dwarf, rose | 3.5 |
| Intergeneric hybrid of Z. elegans and T. erecta | 8192-14 | semi-dwarf, rose | 3.5 |
| Intergeneric hybrid of Z. elegans and T. erecta | 8192-15 | semi-dwarf, rose | 3.5 |
| Intergeneric hybrid of Z. elegans and T. erecta | 8192-16 | tall, rose | 3.5 |
| Intergeneric hybrid of Z. elegans and T. erecta | 8192-17 | tall, rose | 3.5 |
| Intergeneric hybrid of Z. elegans and T. erecta | 8193-1 | dwarf, cream | 4.5 |
| Intergeneric hybrid of Z. elegans and T. erecta | 8193-2 | dwarf, cream | 4.5 |
| Intergeneric hybrid of Z. elegans and T. erecta | 8193-3 | dwarf, cream | 4.5 |
| Intergeneric hybrid of Z. elegans and T. erecta | 8193-4 | dwarf, yellow | 4.5 |
| Intergeneric hybrid of Z. elegans and T. erecta | 8193-5 | dwarf, yellow | 4.5 |
| Intergeneric hybrid of Z. elegans and T. erecta | 8193-6 | dwarf, yellow | 4.5 |
| Intergeneric hybrid of Z. elegans and T. erecta | 8193-7 | dwarf, yellow | 4.5 |
| Intergeneric hybrid of Z. elegans and T. erecta | 8193-8 | dwarf, yellow | 4.5 |
| Intergeneric hybrid of Z. elegans and T. erecta | 8193-9 | dwarf, yellow | 4.5 |
| Intergeneric hybrid of Z. elegans and T. erecta | 8193-10 | dwarf, yellow | 4.5 |
| Intergeneric hybrid of Z. elegans and T. erecta | 8193-11 | dwarf, yellow | 4.5 |
| Intergeneric hybrid of Z. elegans and T. erecta | 8193-12 | dwarf, yellow | 4.5 |
| Intergeneric hybrid of Z. elegans and T. erecta | 8193-13 | dwarf, yellow | 4.5 |
| Intergeneric hybrid of Z. elegans and T. erecta | 8193-14 | dwarf, yellow | 4.5 |
| Intergeneric hybrid of Z. elegans and T. erecta | 8193-15 | dwarf, yellow | 4.5 |
| Intergeneric hybrid of Z. elegans and T. erecta | 8193-16 | dwarf, yellow | 4.5 |
| Intergeneric hybrid of Z. elegans and T. erecta | 8193-17 | dwarf, yellow | 4.5 |
| Intergeneric hybrid of Z. elegans and T. erecta | 8193-18 | dwarf, yellow | 4.5 |
| Intergeneric hybrid of Z. elegans and T. erecta | 8193-19 | dwarf, yellow | 4.5 |
| Intergeneric hybrid of Z. elegans and T. erecta | 8193-20 | dwarf, yellow | 4.5 |
| Intergeneric hybrid of Z. elegans and T. erecta | 8193-21 | ms, tall | 4.5 |
| Intergeneric hybrid of Z. elegans and T. erecta | 8193-22 | tall, yellow | 4.5 |
| Intergeneric hybrid of Z. elegans and T. erecta | 8193-23 | tall, yellow | 4.5 |
| Intergeneric hybrid of Z. elegans and T. erecta | 8193-24 | tall, yellow | 4.5 |
| Intergeneric hybrid of Z. elegans and T. erecta | 8193-25 | tall, yellow | 4.5 |
| Intergeneric hybrid of Z. elegans and T. erecta | 8193-26 | tall, yellow | 4.5 |
| Intergeneric hybrid of Z. elegans and T. erecta | 8193-27 | tall, yellow | 4.5 |
| Intergeneric hybrid of Z. elegans and T. erecta | 8193-28 | tall, yellow | 4.5 |
| Intergeneric hybrid of Z. elegans and T. erecta | 8193-29 | tall, yellow | 4.5 |
| Intergeneric hybrid of Z. elegans and T. erecta | 8194-1 | dwarf, white | 5 |
| Intergeneric hybrid of Z. elegans and T. erecta | 8194-2 | dwarf, white | 5 |
| Intergeneric hybrid of Z. elegans and T. erecta | 8194-3 | dwarf, white | 5 |
| Intergeneric hybrid of Z. elegans and T. erecta | 8194-4 | dwarf, white | 5 |
| Intergeneric hybrid of Z. elegans and T. erecta | 8194-5 | dwarf, white | 5 |
| Intergeneric hybrid of Z. elegans and T. erecta | 8194-6 | dwarf, white | 5 |
| Intergeneric hybrid of Z. elegans and T. erecta | 8194-7 | dwarf, white | 5 |
| Intergeneric hybrid of Z. elegans and T. erecta | 8194-8 | dwarf, ms | 5 |
| Intergeneric hybrid of Z. elegans and T. erecta | 8194-9 | dwarf, ms | 5 |
| Intergeneric hybrid of Z. elegans and T. erecta | 8194-10 | dwarf, ms | 5 |
| Intergeneric hybrid of Z. elegans and T. erecta | 8194-11 | dwarf, ms | 5 |
| Intergeneric hybrid of Z. elegans and T. erecta | 8194-12 | semi-dwarf, white | 5 |
| Intergeneric hybrid of Z. elegans and T. erecta | 8194-13 | semi-dwarf, white | 5 |
| Intergeneric hybrid of Z. elegans and T. erecta | 8194-14 | semi-dwarf, white | 5 |
| Intergeneric hybrid of Z. elegans and T. erecta | 8194-15 | semi-dwarf, white | 5 |
| Intergeneric hybrid of Z. elegans and T. erecta | 8194-16 | semi-dwarf, white | 5 |
| Intergeneric hybrid of Z. elegans and T. erecta | 8194-17 | semi-dwarf, white | 5 |
| Intergeneric hybrid of Z. elegans and T. erecta | 8194-18 | semi-dwarf, white | 5 |
| Intergeneric hybrid of Z. elegans and T. erecta | 8194-19 | semi-dwarf, white | 5 |
| Intergeneric hybrid of Z. elegans and T. erecta | 8194-20 | semi-dwarf, white | 5 |
| Intergeneric hybrid of Z. elegans and T. erecta | 8194-21 | semi-dwarf, white | 5 |
| Intergeneric hybrid of Z. elegans and T. erecta | 8194-22 | semi-dwarf, white | 5 |
| Intergeneric hybrid of Z. elegans and T. erecta | 8194-23 | semi-dwarf, white | 5 |
| Intergeneric hybrid of Z. elegans and T. erecta | 8194-24 | tall, ms | 5 |
| Intergeneric hybrid of Z. elegans and T. erecta | 8194-25 | tall, ms | 5 |
| Intergeneric hybrid of Z. elegans and T. erecta | 8194-26 | tall, ms | 5 |
| Intergeneric hybrid of Z. elegans and T. erecta | 8194-27 | tall, yellow | 5 |
| Intergeneric hybrid of Z. elegans and T. erecta | 8194-28 | tall, yellow | 5 |
| Intergeneric hybrid of Z. elegans and T. erecta | 8194-29 | tall, white | 5 |
| Intergeneric hybrid of Z. elegans and T. erecta | 8194-30 | tall, white | 5 |
| Intergeneric hybrid of Z. elegans and T. erecta | 8194-31 | tall, white | 5 |
| Intergeneric hybrid of Z. elegans and T. erecta | 8194-32 | tall, white | 5 |
| Intergeneric hybrid of Z. elegans and T. erecta | 8194-33 | tall, white | 5 |
| Intergeneric hybrid of Z. elegans and T. erecta | 8194-34 | tall, white | 5 |
| Intergeneric hybrid of Z. elegans and T. erecta | 8195-1 | semi-dwarf, ms | 5 |
| Intergeneric hybrid of Z. elegans and T. erecta | 8195-2 | semi-dwarf, ms | 5 |

TABLE 2-continued

| Genus species | Name | Description | Powdery mildew expression (1 high mildew - 5 least mildew) |
|---|---|---|---|
| Intergeneric hybrid of Z. elegans and T. erecta | 8195-3 | semi-dwarf, ms | 5 |
| Intergeneric hybrid of Z. elegans and T. erecta | 8195-4 | semi-dwarf, ms | 5 |
| Intergeneric hybrid of Z. elegans and T. erecta | 8195-5 | semi-dwarf, ms | 5 |
| Intergeneric hybrid of Z. elegans and T. erecta | 8195-6 | semi-dwarf, vase shape, branched, yellow | 5 |
| Intergeneric hybrid of Z. elegans and T. erecta | 8195-7 | semi-dwarf, vase shape, branched, yellow | 5 |
| Intergeneric hybrid of Z. elegans and T. erecta | 8195-8 | semi-dwarf, vase shape, branched, yellow | 5 |
| Intergeneric hybrid of Z. elegans and T. erecta | 8195-9 | semi-dwarf, vase shape, branched, yellow | 5 |
| Intergeneric hybrid of Z. elegans and T. erecta | 8195-10 | semi-dwarf, vase shape, branched, yellow | 5 |
| Intergeneric hybrid of Z. elegans and T. erecta | 8195-11 | semi-dwarf, vase shape, branched, yellow | 5 |
| Intergeneric hybrid of Z. elegans and T. erecta | 8195-12 | semi-dwarf, vase shape, branched, yellow | 5 |
| Intergeneric hybrid of Z. elegans and T. erecta | 8195-13 | semi-dwarf, vase shape, branched, yellow | 5 |
| Intergeneric hybrid of Z. elegans and T. erecta | 8195-14 | semi-dwarf, vase shape, branched, yellow | 5 |
| Intergeneric hybrid of Z. elegans and T. erecta | 8195-15 | semi-dwarf, vase shape, branched, yellow | 5 |
| Intergeneric hybrid of Z. elegans and T. erecta | 8195-16 | semi-dwarf, yellow | 5 |
| Intergeneric hybrid of Z. elegans and T. erecta | 8195-17 | semi-dwarf, yellow | 5 |
| Intergeneric hybrid of Z. elegans and T. erecta | 8195-18 | semi-dwarf, yellow | 5 |
| Intergeneric hybrid of Z. elegans and T. erecta | 8195-19 | semi-dwarf, yellow | 5 |
| Intergeneric hybrid of Z. elegans and T. erecta | 8195-20 | semi-dwarf, yellow | 5 |
| Intergeneric hybrid of Z. elegans and T. erecta | 8195-21 | semi-dwarf, yellow | 5 |
| Intergeneric hybrid of Z. elegans and T. erecta | 8195-22 | semi-dwarf, yellow | 5 |
| Intergeneric hybrid of Z. elegans and T. erecta | 8195-23 | semi-dwarf, yellow | 5 |
| Intergeneric hybrid of Z. elegans and T. erecta | 8195-24 | semi-dwarf, yellow | 5 |
| Intergeneric hybrid of Z. elegans and T. erecta | 8195-25 | semi-dwarf, yellow | 5 |
| Intergeneric hybrid of Z. elegans and T. erecta | 8195-26 | semi-dwarf, yellow | 5 |
| Intergeneric hybrid of Z. elegans and T. erecta | 8195-27 | semi-dwarf, yellow | 5 |
| Intergeneric hybrid of Z. elegans and T. erecta | 8195-28 | semi-dwarf, yellow | 5 |
| Intergeneric hybrid of Z. elegans and T. erecta | 8195-29 | semi-dwarf, yellow | 5 |
| Intergeneric hybrid of Z. elegans and T. erecta | 8195-30 | semi-dwarf, yellow | 5 |
| Intergeneric hybrid of Z. elegans and T. erecta | 8195-31 | semi-dwarf, yellow | 5 |
| Intergeneric hybrid of Z. elegans and T. erecta | 8195-32 | semi-dwarf, yellow | 5 |
| Intergeneric hybrid of Z. elegans and T. erecta | 8196-1 | dwarf, ms | 3.5 |
| Intergeneric hybrid of Z. elegans and T. erecta | 8196-2 | dwarf, ms | 3.5 |
| Intergeneric hybrid of Z. elegans and T. erecta | 8196-3 | dwarf, ms | 3.5 |
| Intergeneric hybrid of Z. elegans and T. erecta | 8196-4 | dwarf, ms | 3.5 |
| Intergeneric hybrid of Z. elegans and T. erecta | 8196-5 | dwarf, ms | 3.5 |
| Intergeneric hybrid of Z. elegans and T. erecta | 8196-6 | dwarf, ms | 3.5 |
| Intergeneric hybrid of Z. elegans and T. erecta | 8196-7 | dwarf, ms | 3.5 |
| Intergeneric hybrid of Z. elegans and T. erecta | 8196-8 | dwarf, ms | 3.5 |
| Intergeneric hybrid of Z. elegans and T. erecta | 8196-9 | dwarf, ms | 3.5 |
| Intergeneric hybrid of Z. elegans and T. erecta | 8196-10 | dwarf, ms | 3.5 |
| Intergeneric hybrid of Z. elegans and T. erecta | 8196-11 | dwarf, ms | 3.5 |
| Intergeneric hybrid of Z. elegans and T. erecta | 8196-12 | dwarf, ms | 3.5 |
| Intergeneric hybrid of Z. elegans and T. erecta | 8196-13 | dwarf, ms | 3.5 |
| Intergeneric hybrid of Z. elegans and T. erecta | 8196-14 | dwarf, ms | 3.5 |
| Intergeneric hybrid of Z. elegans and T. erecta | 8196-15 | dwarf, coral orange | 3.5 |
| Intergeneric hybrid of Z. elegans and T. erecta | 8196-16 | dwarf, coral orange | 3.5 |
| Intergeneric hybrid of Z. elegans and T. erecta | 8196-17 | dwarf, coral orange | 3.5 |
| Intergeneric hybrid of Z. elegans and T. erecta | 8196-18 | dwarf, coral orange | 3.5 |
| Intergeneric hybrid of Z. elegans and T. erecta | 8196-19 | dwarf, coral orange | 3.5 |
| Intergeneric hybrid of Z. elegans and T. erecta | 8196-20 | dwarf, coral orange | 3.5 |
| Intergeneric hybrid of Z. elegans and T. erecta | 8196-21 | dwarf, coral orange | 3.5 |
| Intergeneric hybrid of Z. elegans and T. erecta | 8196-22 | dwarf, coral orange | 3.5 |
| Intergeneric hybrid of Z. elegans and T. erecta | 8196-23 | dwarf, coral orange | 3.5 |
| Intergeneric hybrid of Z. elegans and T. erecta | 8196-24 | dwarf, coral orange | 3.5 |
| Intergeneric hybrid of Z. elegans and T. erecta | 8196-25 | dwarf, coral orange | 3.5 |
| Intergeneric hybrid of Z. elegans and T. erecta | 8196-26 | dwarf, coral orange | 3.5 |
| Intergeneric hybrid of Z. elegans and T. erecta | 8196-27 | dwarf, coral orange | 3.5 |
| Intergeneric hybrid of Z. elegans and T. erecta | 8196-28 | dwarf, pink | 3.5 |
| Intergeneric hybrid of Z. elegans and T. erecta | 8196-29 | dwarf, pink | 3.5 |
| Intergeneric hybrid of Z. elegans and T. erecta | 8196-30 | dwarf, pink | 3.5 |
| Intergeneric hybrid of Z. elegans and T. erecta | 8196-31 | dwarf, pink | 3.5 |
| Intergeneric hybrid of Z. elegans and T. erecta | 8196-32 | dwarf, pink | 3.5 |

TABLE 2-continued

| Genus species | Name | Description | Powdery mildew expression (1 high mildew - 5 least mildew) |
|---|---|---|---|
| Intergeneric hybrid of Z. elegans and T. erecta | 8196-33 | dwarf, pink | 3.5 |
| Intergeneric hybrid of Z. elegans and T. erecta | 8196-34 | dwarf, pink | 3.5 |
| Intergeneric hybrid of Z. elegans and T. erecta | 8196-35 | dwarf, pink | 3.5 |
| Intergeneric hybrid of Z. elegans and T. erecta | 8196-36 | dwarf, pink | 3.5 |
| Intergeneric hybrid of Z. elegans and T. erecta | 8196-37 | dwarf, pink | 3.5 |
| Intergeneric hybrid of Z. elegans and T. erecta | 8196-38 | dwarf, pink | 3.5 |
| Intergeneric hybrid of Z. elegans and T. erecta | 8196-39 | dwarf, pink | 3.5 |
| Intergeneric hybrid of Z. elegans and T. erecta | 8196-40 | dwarf, pink | 3.5 |
| Intergeneric hybrid of Z. elegans and T. erecta | 8196-41 | dwarf, pink | 3.5 |
| Intergeneric hybrid of Z. elegans and T. erecta | 8196-42 | dwarf, pink | 3.5 |
| Intergeneric hybrid of Z. elegans and T. erecta | 8196-43 | dwarf, pink | 3.5 |
| Intergeneric hybrid of Z. elegans and T. erecta | 8196-44 | dwarf, pink | 3.5 |
| Intergeneric hybrid of Z. elegans and T. erecta | 8196-45 | dwarf, pink | 3.5 |
| Z. elegans | 1778-1* | gold-red bicolor, ms | 1 |
| Z. elegans | 1778-2* | gold-red bicolor, ms | 1 |
| Z. elegans | 1778-3* | gold-red bicolor, ms | 1 |
| Z. elegans | 1778-4* | gold-red bicolor, ms | 1 |
| Z. elegans | 1778-5* | gold-red bicolor, ms | 1 |
| Z. elegans | 1778-6* | gold-red bicolor, ms | 1 |
| Z. elegans | 1778-7* | gold-red bicolor, ms | 1 |
| Z. elegans | 1778-8* | gold-red bicolor, ms | 1 |
| Z. elegans | 1778-9* | gold-red bicolor, ms | 1 |
| Z. elegans | 1778-10* | gold-red bicolor, ms | 1 |
| Z. elegans | 1778-11* | gold-red bicolor, ms | 1 |
| Z. elegans | 1778-12* | gold-red bicolor, ms | 1 |
| Z. elegans | 1778-13* | gold-red bicolor, ms | 1 |
| Z. elegans | 1778-14* | gold-red bicolor, ms | 1 |
| Z. elegans | 1778-15* | gold-red bicolor, ms | 1 |
| Z. elegans | 1780-1* | gold-red bicolor, ms | 1 |
| Z. elegans | 1780-2* | gold-red bicolor, ms | 1 |
| Z. elegans | 1780-3* | gold-red bicolor, ms | 1 |
| Z. elegans | 1780-4* | gold-red bicolor, ms | 1 |
| Z. elegans | 1780-5* | gold-red bicolor, ms | 1 |
| Z. elegans | 1780-6* | gold-red bicolor, ms | 1 |
| Z. elegans | 1795-1* | red, ms | 2 |
| Z. elegans | 1795-2* | red, ms | 2 |
| Z. elegans | 1795-3* | red, ms | 2 |
| Z. elegans | 1795-4* | red, ms | 2 |
| Z. elegans | 1795-5* | red, ms | 2 |
| Z. elegans | 1795-6* | red, ms | 2 |
| Z. elegans | 1795-7* | red, ms | 2 |
| Z. elegans | 1795-8* | red | 2 |
| Z. elegans | 1795-9* | red | 2 |
| Z. elegans | 1795-10* | red | 2 |
| Z. elegans | 1795-11* | red | 2 |
| Z. elegans | 1795-12* | red | 2 |
| Z. elegans | 1795-13* | red | 2 |
| Z. elegans | 1795-14* | red | 2 |
| Z. elegans | 1797-1* | red, ms | 2 |
| Z. elegans | 1797-2* | red, ms | 2 |
| Z. elegans | 1797-3* | red, ms | 2 |
| Z. elegans | 1797-4* | red, ms | 2 |
| Z. elegans | 1797-5* | red | 2 |
| Z. elegans | 1798-1* | red, ms | 2 |
| Z. elegans | 1798-2* | red, ms | 2 |
| Z. elegans | 1798-3* | red, ms | 2 |
| Z. elegans | 1798-4* | red, ms | 2 |
| Z. elegans | 1798-5* | red, ms | 2 |
| Z. elegans | 1798-6* | red, ms | 2 |
| Z. elegans | 1798-7* | red | 2 |
| Z. elegans | 1798-8* | red | 2 |
| Z. elegans | 1798-9* | red | 2 |
| Z. elegans | 1798-10* | red | 2 |
| Z. elegans | 1798-11* | red | 2 |
| Z. elegans | 1798-12* | red | 2 |
| Z. elegans | 1798-13* | red | 2 |
| Z. elegans | 1798-14* | red | 2 |
| Z. elegans | 1798-15* | red | 2 |
| Z. elegans | 1798-16* | red | 2 |
| Z. elegans | 1799-1* | red, ms | 2 |
| Z. elegans | 1799-2* | red, ms | 2 |
| Z. elegans | 1811-1* | red-white bicolor, ms | 3 |
| Z. elegans | 1811-2* | red-white bicolor, ms | 3 |
| Z. elegans | 1811-3* | red-white bicolor, ms | 3 |
| Z. elegans | 1811-4* | red-white bicolor, ms | 3 |
| Z. elegans | 1811-5* | red-white bicolor, ms | 3 |
| Z. elegans | 1811-6* | red-white bicolor, ms | 3 |
| Z. elegans | 1811-7* | red-white bicolor, ms | 3 |
| Z. elegans | 1811-8* | red-white bicolor, ms | 3 |
| Z. elegans | 1811-9* | red-white bicolor, ms | 3 |
| Z. elegans | 1631-1 | purple, fertile | 3 |
| Z. elegans | 1631-2 | purple, fertile | 3 |
| Z. elegans | 1631-3 | purple, fertile | 3 |
| Z. elegans | 1631-4 | purple, fertile | 3 |
| Z. elegans | 1631-5 | purple, fertile | 3 |
| Z. elegans | 1631-6 | purple, fertile | 3 |
| T. erecta | 1653 m* | white, dwarf | 5 |

As shown in Table 2, the intergeneric hybrid plants of Z. elegans and T. erecta have mildew expression ratings with an average of 4.5, indicating that they have the least mildew. In contrast, the straight genera of Z. elegans have powdery mildew expression ratings with an average of 1.9, indicating that they have more mildew. T. erecta had a powdery mildew expression rating of 5, indicating the least mildew. The results indicate that the intergeneric cross unexpectedly improves the powdery mildew expression compared to Z. elegans plants.

Additionally, segregating populations of primary intergeneric crosses and backcrosses in both directions to recurrent parents were evaluated for the effects on performance of field horticultural traits as well as disease resistance. Primary intergeneric hybrids of *T. erecta*×*Z. elegans* with *T. erecta* as the female parent unexpectedly looked completely clean of disease and showed a very nice spreading dome type habit not typical of the parent plant habit. In backcross populations using the primary intergeneric hybrid *Z. elegans*×*T. erecta*, there were different expressions of disease tolerance depending on the recurrent parent used for the backcross. Segregates have been seen out of backcross populations that showed strong and intermediate resistance to powdery mildew and fungal spot. When the backcross involved the *Z. elegans* parent, the resulting population showed about 50% surviving plants with varying degrees of powdery mildew. When the backcross involved the *T. erecta* parent, the populations showed less than 20% plant death, with some individuals completely clean and the majority showed varying degrees of powdery mildew infection.

Table 3 shows over 60 other examples of intergeneric hybrid plants of *Z. elegans* and *T. erecta* produced by the method of the invention in 2015 and the parent plants used in the crosses, including reciprocal crosses, the addition of *T. patula* (French marigold) and the use of intergeneric hybrid plants as one or both of the parents. Column 1 shows the genus and species of the female parent, column 2 shows the name of the female parent, column 3 shows a brief description of the female parent, column 4 shows the genus and species of the male parent, column 5 shows the name of the male parent, column 6 shows a brief description of the male parent, column 7 shows the name of the *Z. elegans* and *T. erecta* intergeneric hybrid produced in the cross and column 8 shows a brief description of the intergeneric hybrid plant. In Table 3, "m" indicates that a mass of plants was made for pollination and harvest of seed, "ms" indicates male sterile, "African" indicates African marigold (*T. erecta*), "French" indicates French marigold (*T. patula*) and an asterisk (*) indicates that the line will segregate for the male sterile (ms) condition, as described above. When a color is listed, it indicates the flower color unless described otherwise, and when "early" or "late" are listed, it indicates early or late to first flower.

TABLE 3

| Female parent genus species | Female parent name | Description of female parent | Male parent genus species | Male parent name | Description of male parent | Intergeneric hybrid name | Description of intergeneric hybrid |
|---|---|---|---|---|---|---|---|
| *T. erecta* | 1653-m* ms | white, dwarf | *Z. elegans* | 1631-1* | purple, fertile | 8332-1 | rusty orange, African-looking, early |
| *T. erecta* | 1653-m* ms | white, dwarf | *Z. elegans* | 1631-1* | purple, fertile | 8332-2 | yellow, African-looking, early |
| *T. erecta* | 1653-m* ms | white, dwarf | *Z. elegans* | 1798-7* | red, fertile | 8333 | white, African-looking, early |
| *Z. elegans* | 1798-5 | purple, fertile | *T. patula* | 8031 | red, semi-double flower, fertile | 8613* | scarlet |
| *Z. elegans* | 1798-5 | red/white bicolor, ms | *T. erecta* | 1653-m* fertile | white, dwarf | 8336 | dwarf, pink, short, fertile |
| *Z. elegans* | 1811-4 | red/gold bicolor, ms | *T. erecta* | 1653-m* fertile | white, dwarf | 8337 | segregated ms, purple, dwarf; fertile, purple, short nodes |
| *Z. elegans* | 1778-ms | red/gold bicolor, ms | intergeneric *Z. elegans* x *T. erecta* | 8191-24 | white, semi-dwarf | 8331 | segregated pink red, short nodes, very dwarf, early, yellow |
| *Z. elegans* | 1778-ms | red/gold bicolor, ms | intergeneric *Z. elegans* x *T. erecta* | 8192-9 | yellow, dwarf | 8325 | segregated pink red, short nodes, very dwarf, yellow |
| *Z. elegans* | 1778-ms | red/gold bicolor, ms | intergeneric *Z. elegans* x *T. erecta* | 8193-7 | yellow, dwarf | 8319a | segregated dwarf, orange bicolor, early, yellow |
| *Z. elegans* | 1778-ms | red/gold bicolor, ms | intergeneric *Z. elegans* x *T. erecta* | 8193-7 | yellow, dwarf | 8319b | segregated tall, orange bicolor, early, yellow |
| *Z. elegans* | 1778-ms | red/gold bicolor, ms | intergeneric *Z. elegans* x *T. erecta* | 8194-14 | white, semi-dwarf | 8313 | segregated purple, short nodes, tall, early, yellow |
| *Z. elegans* | 1778-ms | red/gold bicolor, ms | intergeneric *Z. elegans* x *T. erecta* | 8195-8 | yellow, semi-dwarf | 8306 | segregated orange, dwarf, early, yellow |
| *Z. elegans* | 1778-ms* | red, fertile | intergeneric *Z. elegans* x *T. erecta* | 8196-17 | coral, dwarf | 8300 | orange bicolor, segregated |

TABLE 3-continued

| Female parent genus species | Female parent name | Description of female parent | Male parent genus species | Male parent name | Description of male parent | Intergeneric hybrid name | Description of intergeneric hybrid |
|---|---|---|---|---|---|---|---|
| Z. elegans | 1795-1* | red, fertile | intergeneric Z. elegans x T. erecta | 8196-16 | coral, dwarf | 8299 | dwarf-semi-dwarf dwarf, orange, fertile |
| Z. elegans | 1795-2* | red, fertile | intergeneric Z. elegans x T. erecta | 8195-7 | yellow, semi-dwarf | 8305 | segregated orange bicolor, dwarf, early, yellow |
| Z. elegans | 1795-3* | red, fertile | intergeneric Z. elegans x T. erecta | 8194-13 | white, semi-dwarf | 8312 | red, fertile, dwarf |
| Z. elegans | 1795-4* | red, fertile | intergeneric Z. elegans x T. erecta | 8193-6 | yellow, dwarf | 8318 | orange bicolor, dwarf - semi-dwarf |
| Z. elegans | 1795-5* | red, fertile | intergeneric Z. elegans x T. erecta | 8192-8 | rose, semi-dwarf | 8324 | segregated semi-dwarf, purple red, short nodes |
| Z. elegans | 1795-6* | red, fertile | intergeneric Z. elegans x T. erecta | 8191-23 | white, semi-dwarf | 8330 | segregated semi-dwarf, purple red, short nodes |
| intergeneric Z. elegans x T. erecta | 8195-3 | yellow, semi-dwarf, ms | intergeneric Z. elegans x T. erecta | 8196-18 | coral orange, dwarf | 8338 | very poor germination, orange yellow, short dwarf |
| intergeneric Z. elegans x T. erecta | 8195-3 | yellow, semi-dwarf, ms | intergeneric Z. elegans x T. erecta | 8194-13 | white, semi-dwarf | 8609 | segregated yellow, white, orange, dwarf, apetalous |
| intergeneric Z. elegans x T. erecta | 8196-2 | coral orange, dwarf, ms | Z. elegans | 1631-fertile* | purple, fertile | 8295 | dwarf, purple |
| intergeneric Z. elegans x T. erecta | 8196-3 | coral orange, dwarf, ms | Z. elegans | 1778-fertile | red/gold bicolor, fertile | 8296 | dwarf, orange bicolor |
| intergeneric Z. elegans x T. erecta | 8195-3 | coral orange, dwarf, ms | Z. elegans | 1778-fertile | red/gold bicolor, fertile | 8303 | dwarf, purple |
| intergeneric Z. elegans x T. erecta | 8192-6 | semi-dwarf, ms | Z. elegans | 1778-fertile | red/gold bicolor, fertile | 8322 | segregated red, short nodes, dwarf, early, yellow |
| intergeneric Z. elegans x T. erecta | 8195-2 | coral orange, dwarf, ms | Z. elegans | 1631-fertile* | purple, fertile | 8302 | semi-dwarf, purple |
| intergeneric Z. elegans x T. erecta | 8192-6 | semi-dwarf, ms | Z. elegans | 1631-fertile* | purple, fertile | 8321 | semi-dwarf, purple |
| intergeneric Z. elegans x T. erecta | 8191-41 | semi-dwarf, ms | Z. elegans | 1631-fertile* | purple, fertile | 8327 | semi-dwarf, purple |
| intergeneric Z. elegans x T. erecta | 8191-42 | semi-dwarf, ms | Z. elegans | 1778-fertile | red/gold bicolor, fertile | 8328 | scarlet, semi-dwarf |
| intergeneric Z. elegans x T. erecta | 8194-25 | tall, ms | Z. elegans | 1631-fertile* | purple, fertile | 8308 | tall, purple |
| intergeneric Z. elegans x T. erecta | 8193-21 | tall, ms | Z. elegans | 1631-fertile* | purple, fertile | 8315 | tall, purple, short nodes |
| intergeneric Z. elegans x T. erecta | 8194-26 | tall, ms | Z. elegans | 1778-fertile | red/gold bicolor, fertile | 8309 | 1 tall, orange bicolor |
| intergeneric Z. elegans x T. erecta | 8193-21 | tall, ms | Z. elegans | 1778-fertile | red/gold bicolor, fertile | 8316 | semi-dwarf, yellow |
| intergeneric Z. elegans x T. erecta | 8195-5 | semi-dwarf, ms | intergeneric Z. elegans x T. erecta | 8192-8 | rose, semi-dwarf | 8611 | |
| intergeneric Z. elegans x T. erecta | 8195-4 | semi-dwarf, ms | intergeneric Z. elegans x T. erecta | 8193-6 | yellow, dwarf | 8610 | yellow, semi-dwarf, fertile |

TABLE 3-continued

| Female parent genus species | Female parent name | Description of female parent | Male parent genus species | Male parent name | Description of male parent | Intergeneric hybrid name | Description of intergeneric hybrid |
|---|---|---|---|---|---|---|---|
| intergeneric Z. elegans x T. erecta | 8195-5* | white, dwarf | intergeneric Z. elegans x T. erecta | 8191-23 | white, semi-dwarf | 8612 | cream white, dwarf, segregates apetalous |
| T. erecta | 1653-m* ms | white, dwarf | intergeneric Z. elegans x T. erecta | 8192-7 | white, dwarf | 8323 | segregated yellow, French-looking, early, yellow, ms, fertile, white, African-looking, late seedlings segregated stem color orange, segregated very early yellow, yellow dwarf, and dwarf, late |
| T. erecta | 1653-m* ms | white, dwarf | intergeneric Z. elegans x T. erecta | 8193-5 | yellow, dwarf | 8317 | |
| T. erecta | 1653-m* ms | white, dwarf | intergeneric Z. elegans x T. erecta | 8194-12 | white, semi-dwarf | 8311a | rusty orange, French-looking, very early |
| T. erecta | 1653-m* ms | white, dwarf | intergeneric Z. elegans x T. erecta | 8194-12 | white, semi-dwarf | 8311b | segregated yellow, French looking, very early, white, African-looking, fertile |
| T. erecta | 1653-m* ms | white, dwarf | intergeneric Z. elegans x T. erecta | 8195-6 | yellow, semi-dwarf | 8304 | segregated yellow, French looking, early, white, African looking, late, fertile |
| T. erecta | 1653-m* ms | white, dwarf | intergeneric Z. elegans x T. erecta | 8196-15 | coral orange, dwarf | 8298 | segregated yellow, French looking, early, white, African looking, segregated ms fertile |
| intergeneric Z. elegans x T. erecta | 8196-4 | coral orange, dwarf, ms | T. erecta | 1698 fertile | tall, garland gold, fertile | 8297 | dwarf, orange |
| intergeneric Z. elegans x T. erecta | 8195-1 | semi-dwarf, ms | T. erecta | 1653-m* fertile | white, dwarf | 8301 | semi-dwarf, yellow |
| intergeneric Z. elegans x T. erecta | 8192-6 | semi-dwarf, ms | T. erecta | 1653-m* fertile | white, dwarf | 8320 | |
| intergeneric Z. elegans x T. erecta | 8191-40 | semi dwarf ms | T. erecta | 1653-m* fertile | white dwarf | 8326 | segregated orange scarlet bicolor, dwarf, red, short nodes, dwarf, fertile |
| intergeneric Z. elegans x T. erecta | 8194-26 | tall ms | T. erecta | 1698 fertile | tall garland gold fertile | 8310-1 | 1-2 ms, dwarf |
| intergeneric Z. elegans x T. erecta | 8194-26 | tall, ms | T. erecta | 1698 fertile | tall, garland gold, fertile | 8310-3 | 3-4 pink, dwarf |
| intergeneric Z. elegans x T. erecta | 8194-26 | tall, ms | T. erecta | 1698 fertile | tall, garland gold, fertile | 8310-a | white, dwarf, prostrate |
| intergeneric Z. elegans x T. erecta | 8194-26 | tall, ms | T. erecta | 1698 fertile | tall, garland gold, fertile | 8310-b | yellow, dwarf, prostrate |
| intergeneric Z. elegans x T. erecta | 8194-24 | tall, ms | T. erecta | 1653-m* fertile | white, dwarf | 8307-1 | 1 ms, tall, yellow |

TABLE 3-continued

| Female parent genus species | Female parent name | Description of female parent | Male parent genus species | Male parent name | Description of male parent | Intergeneric hybrid name | Description of intergeneric hybrid |
|---|---|---|---|---|---|---|---|
| intergeneric Z. elegans x T. erecta | 8194-24 | tall, ms | T. erecta | 1653-m* | white, fertile | 8307-2 | 2 yellow, semi-dwarf |
| intergeneric Z. elegans x T. erecta | 8193-21 | tall, ms | T. erecta | 1653-m* | white, fertile | 8314 | yellow, semi-dwarf, fertile |
| Z. elegans | 1792-1,2 ms* | red, dwarf, ms | T. erecta | 1494-4,3 fertile* | orange, dwarf, ms | 9091* | red, zinnia-looking, dwarf |
| Z. elegans | 1796-1,2 ms* | red, dwarf, ms | T. erecta | 1497-2,1 fertile* | orange, dwarf, ms | 9092* | red, zinnia-looking, dwarf |
| Z. elegans | 1803-1,2 ms* | red, dwarf, ms | T. erecta | 1500-2,1* fertile | orange, dwarf, ms | 9093* | red, zinnia-looking, dwarf |
| T. erecta | 1497-2,1 ms* | orange, dwarf, ms | Z. elegans | 1796-1,2 fertile* | red, dwarf, ms | 9095 | dwarf, orange, African-looking, ms |
| T. erecta | 1494-4,3 ms* | orange, dwarf, ms | Z. elegans | 1792-1,2 fertile* | red, dwarf, ms | 9094-1 | dwarf, orange, African-looking, ms |
| T. erecta | 1500-2,1ms* | orange, dwarf, ms | Z. elegans | 1803-1,2 fertile* | red, dwarf, ms | 9096 mass a | dwarf, orange, African-looking, ms |
| T. erecta | 1599-2,1 ms* | orange, dwarf, ms | Z. elegans | 1631-1m* | purple, dwarf | 9097 mass a | dwarf, orange, African-looking, ms |
| T. erecta | 1605-2,1 ms* | orange, dwarf, ms | Z. elegans | 1631-1m* | purple, dwarf | 9098 mass a | dwarf, orange, African-looking, ms |
| T. erecta | 1497-2,1 ms* | orange, dwarf, ms | Z. elegans | 1631-1m* | purple, dwarf | 9101-1 | dwarf, orange, African-looking, ms |
| T. erecta | 1500-2,1ms* | orange, dwarf, ms | Z. elegans | 1631-1m* | purple, dwarf | 9102 mass a | dwarf, orange, African-looking, fertile |

As shown in Table 3, numerous intergeneric hybrid plants of Z. elegans and T. erecta have been created, using either genus as the female or male parent. In addition, the intergeneric hybrid plants of Z. elegans and T. erecta were further used in additional crosses to Z. elegans plants, T. erecta plants and other intergeneric hybrid plants of Z. elegans and T. erecta to successfully create further intergeneric hybrid plants of Z. elegans and T. erecta. All backcrosses of the intergeneric hybrid to either the Z. elegans or T. erecta recurrent parent surprisingly germinated approximately 2 days before the inbred lines of those recurrent parents, and overall germination for these backcrosses was very good and greater than 80%.

Unexpectedly, the intergeneric hybrid plants of Z. elegans and T. erecta that were backcrossed to either Z. elegans or T. erecta tended to look very much like the female used in the backcross, even if the backcross was the same combination but reciprocal. Additionally, when a Z. elegans×T. erecta intergeneric hybrid was backcrossed to a female T. erecta, the backcross 1 (BC1) plants segregated between plants that looked like French marigolds and others that were later to flower and looked like African marigolds, such as intergeneric hybrids 8323 and 8304 shown in Table 3.

The use of intergeneric hybrid plants in further crosses to either Z. elegans or T. erecta surprisingly resulted in new and unexpected flower colors and patterns not previously seen in either parent. For example, intergeneric hybrid plants 8319a, 8300 and 8326 each had bicolor flowers representing new expressions of flower color pattern not present in T. erecta. Additionally, backcross populations using T. erecta as the female parent segregated with red pigmented stems, which is a color not present in any of the T. erecta germplasm used by the inventor. Additional trials also saw tri-color flowers in the intergeneric hybrid plants. Surprisingly, all intergeneric hybrid plants of the present invention, whether primary hybrids or backcross hybrids, showed strong heterosis for germination, plant size and earliness.

In these wide intergeneric crosses, a plant breeding technique called congruity backcrossing (CBC) was also employed. The principle behind congruity backcrossing is that when a wide cross is made between species or genera that have not been associated and interbred, the resulting hybrid plants will be hybrid, but will have large blocks of DNA on the chromosomes that will not have been fully recombined with that of the other parent in the cross. The technique of congruity backcrossing was developed to help integrate more fully the genomes of the two disparate parents, break up linkage groups, and help to express desired traits and new traits from new recombinations of genes.

Congruity backcrossing (CBC) involved making the primary cross, A×B→C, and the resulting hybrid was then utilized to cross back to one of the original parents (also known as recurrent parents) each cycle in an alternating fashion. The method of the current invention has employed and progressed congruity backcrossing for up to four or more generations and has seen more variation and expression of traits in the further intergeneric hybrids of Z. elegans and T. erecta produced by this method. The primary cross also began with B×A→C, followed by backcrossing C with B, and continued with the appropriate congruity backcrossing method. The following symbols are used in the congruity backcrossing method, which continued for up to four cycles or more with an example provided below.

a) A=Z. elegans
b) B=T. erecta
c) A×B→C(F1)
d) (C×A)→BC1
e) (BC1×B)→CBC1
f) (CBC1×A)→CBC2
g) (CBC2×B)→CBC3
h) (CBC3×A)→CBC4

Table 4 shows examples of congruity backcrosses used in the method of the invention to produce intergeneric hybrid plants of Z. elegans and T. erecta. In Table 4, column 1 shows the cross, column 2 shows the name, column 3 shows a brief description of the plant produced, and column 4 indicates the cycle of the congruity backcross used. In Table 4, "ms" indicates male sterile and "m" indicates that a mass of plants was made for pollination and harvest of seed.

Flow cytometry is a technique that is used to measure the "weight" of DNA in a given cell. Flow cytometry is commonly utilized when verification of the level of ploidy is needed, such as to distinguish diploid from higher ploidy levels when they are suspected or being analyzed. Table 5 shows quantitative evidence of the combination of Z. elegans and T. erecta and its reciprocal from flow cytometry work performed on intergeneric hybrid plants, backcrosses and parents. Table 5, column 1 shows the pedigree, column 2 shows the source, columns 3-5 show the results of run 1, run 2 and the mean, respectively, and column 6 shows the plant description. In Table 5, "m" indicates that a mass of plants was made for pollination and harvest of seed, "intergeneric" refers to an intergeneric plant of Z. elegans and T. erecta and "ms" indicates male sterile.

TABLE 4

| Cross | Name | Description | CBC cycle |
| --- | --- | --- | --- |
| dwarf, orange T. erecta apetalous (1605-2,1 ms) x dwarf, red, fertile Z. elegans (1796-1,2 fertile) | 9104A | dwarf, orange, African-looking, segregates ms | F1 |
| dwarf, orange, fertile T. erecta (1599-2,1 ms) X [((apetalous, intergeneric hybrid x semi-dwarf, white, fertile T. erecta) x red/gold, dwarf Z. elegans fertile) (8322-1)] | 9118-1 | dwarf, orange, African-looking, segregates ms | CBC2 |
| dwarf, orange, fertile T. erecta (1599-2,1 ms) X [((apetalous, intergeneric hybrid x semi-dwarf, white, fertile T. erecta) x red/gold, dwarf Z. elegans fertile) (8322-1)] | 9118-3 | dwarf, orange, African-looking, segregates ms | CBC2 |
| dwarf, orange, fertile T. erecta (1599-2,1 ms) X [((apetalous, intergeneric hybrid x semi-dwarf, white, fertile T. erecta) x red/gold, dwarf Z. elegans fertile) (8321 m)] | 9120 | dwarf, orange, African-looking, segregates ms | CBC2 |
| dwarf, orange, fertile T. erecta (1599-2,1ms) X [((apetalous, intergeneric hybrid x semi-dwarf, white, fertile T. erecta) x red/gold, dwarf Z. elegans fertile) (8328 m)] | 9121 | dwarf, orange, African-looking, segregates ms | CBC2 |
| dwarf, orange, fertile T. erecta (1609-2,1 ms) X [((apetalous, intergeneric hybrid x semi-dwarf, white, fertile T. erecta) x red/gold, dwarf Z. elegans fertile) (8322-1)] | 9122 | dwarf, orange, African-looking, segregates ms | CBC2 |
| dwarf, orange, fertile T. erecta (1609-2,1 ms) X [((apetalous, intergeneric hybrid x semi-dwarf, white, fertile T. erecta) x red/gold, dwarf Z. elegans fertile) (8327 m)] | 9123 | dwarf, orange, African-looking, segregates ms | CBC2 |
| dwarf, orange, fertile T. erecta (1609-2,1 ms) X [((apetalous, intergeneric hybrid x semi-dwarf, white, fertile T. erecta) x red/gold, dwarf Z. elegans fertile) (8321 m)] | 9124 | dwarf, orange, African-looking, segregates ms | CBC2 |
| dwarf, orange, fertile T. erecta (1609-2,1 ms) X [((apetalous, intergeneric hybrid x semi-dwarf, white, fertile T. erecta) x red/gold, dwarf Z. elegans fertile) (8328 m)] | 9125 | dwarf, orange, African-looking, segregates ms | CBC2 |

TABLE 5

| Pedigree | Source | Run 1 | Run 2 | Mean | Plant description |
|---|---|---|---|---|---|
| 1653-m | T. erecta | 70.93 | 63.2 | 67.07 | pure white, African marigold recurrent parent |
| 8298a | T. erecta recurrent parent ms x intergeneric fertile dwarf | 67.03 | 81.73 | 74.38 | yellow, French-looking |
| 8298 m | T. erecta recurrent parent ms x intergeneric fertile dwarf | 57.25 | 66.44 | 61.85 | white, African-looking |
| 8311-1 | T. erecta recurrent parent ms x intergeneric fertile semi-dwarf white | 107.82 | 106.22 | 107.02 | yellow, French-looking |
| 8311-2 | T. erecta recurrent parent ms x intergeneric fertile semi-dwarf white | 127.56 | 98.95 | 113.26 | rusty orange, African-looking |
| 8311-3 | T. erecta recurrent parent ms x intergeneric fertile semi-dwarf white | 64.9 | 61.27 | 63.09 | white, African-looking |
| 8332-1 | T. erecta recurrent parent ms x Z. elegans red dwarf fertile | 112.37 | 109.18 | 110.78 | gold/red, French marigold looking |
| 8332-2 | T. erecta recurrent parent ms x Z. elegans red dwarf fertile | 51.25 | 49.52 | 50.39 | white, African-looking |
| 1796-1,2 | Z. elegans | 210.57 | 173.39 | 191.98 | red, pure zinnia recurrent parent |
| 8305-1 | Z. elegans dwarf red ms x intergeneric fertile semi-dwarf | 235.18 | 239.24 | 237.21 | orange bicolor, zinnia looking |

As shown in Table 5, the flow cytometry results show that the DNA content of Z. elegans is significantly larger than that of T. erecta. Both genera are reported as diploid with 2n=24 and are the same for the chromosome count. These results indicate that the actual chromosomes in Z. elegans are larger than those of T. erecta. Additionally, the results of the T. erecta and Z. elegans parent plants alone can be compared with the resulting intergeneric hybrids, which have a very different DNA "weight" than that of either parent. Further, the results show that most intergeneric hybrids of the present invention are of intermediate weight between the two parents depending on how they have been utilized.

Further Embodiments of the Invention

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include improved plant habit, new or improved flower color, resistance to diseases and insects, tolerance to drought and heat, better agronomic quality and other horticultural characters like branching, earliness to flower and general plant vigor, which will confer better performance in stressful growing conditions.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

A goal of plant breeding is to develop new, unique, and superior hybrid plants. The breeder initially selects and crosses two or more parental lines, which may be followed by repeated selfing and selection, producing many new genetic combinations. The breeder can theoretically generate billions of different genetic combinations via crossing, selfing, and mutations. The breeder has no direct control at the cellular level. Therefore, no two breeders will select exactly the same combination of traits because of differing expression and individual selection style and preferences.

Each year, the plant breeder selects the germplasm to advance to the next generation. This germplasm is grown under different geographical, climatic, and soil conditions, and further selections are then made during, and at the end of, the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior hybrid plants.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen (Molecular Linkage Map of Soybean (*Glycine max*), pp. 6.131-6.138 in S. J. O'Brien (ed.) *Genetic Maps: Locus Maps of Complex Genomes*, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into plant varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Descriptions of other breeding methods that are commonly used for different traits and crops can be found in one of several reference books (e.g., *Principles of Plant Breeding*, John Wiley and Son, pp. 115-161 (1960); Allard (1960); Simmonds (1979); Sneep, et al. (1979); Fehr (1987); "Carrots and Related Vegetable Umbelliferae," Rubatzky, V. E., et al. (1999).

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed intergeneric hybrid plants of *Z. elegans* and *T. erecta* using transformation methods as described to incorporate transgenes into the genetic material of the plant(s).

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

When the term "intergeneric hybrid plants of *Z. elegans* and *T. erecta*" is used in the context of the present invention, this also includes any gene conversions or locus conversions of that plant. The term "gene converted plant" as used herein refers to those intergeneric hybrid plants of *Z. elegans* and *T. erecta* which are developed by backcrossing, genetic engineering, or mutation, wherein essentially all of the desired morphological and physiological characteristics of a variety are recovered in addition to the one or more genes transferred into the variety via the backcrossing technique, genetic engineering, or mutation.

Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental plant which contributes the gene for the desired characteristic is termed the "nonrecurrent" or "donor parent." This terminology refers to the fact that the nonrecurrent parent is used one time in the backcross protocol and therefore does not recur. The parental plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the transferred gene from the nonrecurrent parent.

Further reproduction of the variety can occur by tissue culture and regeneration. Tissue culture of various tissues and regeneration of plants therefrom is well known and widely published. For example, reference may be had to Teng, et al., *HortScience*, 27:9, 1030-1032 (1992); Teng, et al., *HortScience*, 28:6, 669-1671 (1993); Zhang, et al., *Journal of Genetics and Breeding*, 46:3, 287-290 (1992); Webb, et al., *Plant Cell Tissue and Organ Culture*, 38:1, 77-79 (1994); Curtis, et al., *Journal of Experimental Botany*, 45:279, 1441-1449 (1994); Nagata, et al., *Journal for the American Society for Horticultural Science*, 125:6, 669-672 (2000); and Ibrahim, et al., *Plant Cell Tissue and Organ Culture*, 28(2), 139-145 (1992). It is clear from the literature that the state of the art is such that these methods of obtaining plants are routinely used and have a high rate of success.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

As used herein, the term "plant" includes plant cells, plant protoplasts, plant cell tissue cultures from which intergeneric hybrid plants of *Z. elegans* and *T. erecta* can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. An intergeneric hybrid plant of *Zinnia elegans* and *Tagetes erecta* having a powdery mildew expression rating of at least 3.5 on a scale of 1 to 5 where 5 is the least mildew and that flowers 1-2 weeks earlier than the *Z. elegans* parent plant and the *T. erecta* parent plant.

2. A plant part of the plant of claim 1, wherein said plant part is selected from the group consisting of protoplasts, seed, embryo, pollen, ovules, tissue, and meristematic cells.

3. A method of producing an intergeneric hybrid plant of *Z. elegans* and *T. erecta* having a powdery mildew expression rating of at least 3.5 on a scale of 1 to 5 where 5 is the least mildew and that flowers 1-2 weeks earlier than the *Z. elegans* parent plant and the *T. erecta* parent plant comprising:
    (a) selecting a first plant of *Z. elegans* or *T. erecta* to use as the female parent and a second plant of the other genera to use as the male parent;
    (b) collecting pollen from open flowers on the male parent;
    (c) applying the pollen to receptive female flowers on the female parent indicated in the cross to produce intergeneric hybrid seed;
    (d) harvesting intergeneric hybrid seed of *Z. elegans* and *T. erecta*; and
    (e) growing and selecting said intergeneric hybrid seed of *Z. elegans* and *T. erecta* to produce an intergeneric hybrid plant of *Z. elegans* and *T. erecta* having a powdery mildew expression rating of at least 3.5 on a scale of 1 to 5 where 5 is the least mildew and that flowers 1-2 weeks earlier than the *Z. elegans* parent plant and the *T. erecta* parent plant.

4. The method of claim 3, further comprising using said intergeneric hybrid plant of *Z. elegans* and *T. erecta* in further crosses to *Z. elegans, T erecta* or other intergeneric hybrid plants of *Z. elegans* and *T. erecta* to produce intergeneric hybrid plants of *Z. elegans* and *T. erecta* having a powdery mildew expression rating of at least 3.5 on a scale of 1 to 5 where 5 is the least mildew and that flowers 1-2 weeks earlier than the *Z. elegans* parent plant and the *T. erecta* parent plant.

5. The method of claim 3, wherein the *Z. elegans* or *T. erecta* plant used as the female parent is nuclear male sterile.

6. The method of claim 4, wherein the *Z. elegans, T erecta*, or intergeneric hybrid plant of *Z. elegans* and *T. erecta* plant used as the female parent is nuclear male sterile.

7. A method of producing an intergeneric hybrid plant of *Z. elegans* and *T. erecta* having a powdery mildew expression rating of at least 3.5 on a scale of 1 to 5 where 5 is the least mildew and that flowers 1-2 weeks earlier than the *Z. elegans* parent plant and the *T. erecta* parent plant comprising:
    (a) selecting a plant of *Z. elegans* or *T. erecta* to use as the female parent and a plant of the other genera to use as the male parent in a cross;
    (b) collecting pollen from open flowers on the male parent;
    (c) applying the pollen to receptive female flowers on the female parent indicated in the cross;
    (d) isolating an embryo resulting from the cross by embryo rescue; and
    (e) growing and selecting said embryo to obtain an intergeneric hybrid plant of *Z. elegans* and *T. erecta* having a powdery mildew expression rating of at least 3.5 on a scale of 1 to 5 where 5 is the least mildew and that flowers 1-2 weeks earlier than the *Z. elegans* parent plant and the *T. erecta* parent plant.

8. The intergeneric hybrid plant of claim 1, further comprising at least one transgene.

9. The intergeneric hybrid plant of claim 1, wherein said plant has different flower colors or color patterns when compared to the *Z. elegans* or *T. erecta* parent plants.

10. The intergeneric hybrid plant of claim 1, wherein said plant has a different plant habit when compared to the *Z. elegans* or *T. erecta* parent plants.

* * * * *